(12) United States Patent
Snowball

(10) Patent No.: US 11,013,242 B2
(45) Date of Patent: May 25, 2021

(54) DISINFECTION OF FOODSTUFFS

(71) Applicant: ULTRA BIOTECS LIMITED, Nottinghamshire (GB)

(72) Inventor: Malcolm Robert Snowball, Essex (GB)

(73) Assignee: ULTRA BIOTECS LIMITED, Nottinghamshire (GB)

(*) Notice: Subject to any disclaimer, the term of this patent is extended or adjusted under 35 U.S.C. 154(b) by 204 days.

(21) Appl. No.: 16/091,959

(22) PCT Filed: Mar. 27, 2017

(86) PCT No.: PCT/GB2017/050856
§ 371 (c)(1),
(2) Date: Oct. 5, 2018

(87) PCT Pub. No.: WO2017/174960
PCT Pub. Date: Oct. 12, 2017

(65) Prior Publication Data
US 2019/0116818 A1 Apr. 25, 2019

(30) Foreign Application Priority Data

Apr. 5, 2016 (GB) .................................. 1605853
Aug. 2, 2016 (GB) .................................. 1613333
Mar. 27, 2017 (GB) .................................. 1704802

(51) Int. Cl.
*A61L 2/00* (2006.01)
*B06B 1/00* (2006.01)
(Continued)

(52) U.S. Cl.
CPC ............... *A23B 4/015* (2013.01); *A23B 4/26* (2013.01); *A23L 3/30* (2013.01); *A61L 2/025* (2013.01);
(Continued)

(58) Field of Classification Search
CPC .. A21D 6/00; A21C 14/00; A61L 2/02; A61L 2/025; A61L 2202/181; A61L 2202/182; B65B 55/00; A23L 1/0252
(Continued)

(56) References Cited

U.S. PATENT DOCUMENTS 5,939,115 A * 8/1999 Kounev ................. A22C 21/04
134/131
6,138,698 A 10/2000 Tanaka
(Continued)

FOREIGN PATENT DOCUMENTS

CN 201410785796 12/2014
CN 105750262 7/2016
(Continued)

OTHER PUBLICATIONS

GB Search and Examination Report dated Oct. 31, 2016 for GB Application No. 1613333.2.
(Continued)

*Primary Examiner* — Monzer R Chorbaji
(74) *Attorney, Agent, or Firm* — Benjamin C. Pelletier; Haynes and Boone LLP

(57) ABSTRACT

An apparatus for disinfecting products is disclosed herein. The apparatus comprises a tank for holding a liquid for receiving microorganisms from the products. The tank comprises a barrier separating the tank to provide two regions of liquid, the two regions of liquid comprising a first region and a second region, wherein the first region is arranged to provide an open channel for the liquid through the tank to enable a product to be carried into, along, and out of a flowpath through the channel; and the second region holds liquid adjacent to at least one ultrasonic transducer for providing ultrasonic energy to the product via the liquid in the second region and through the barrier.

9 Claims, 13 Drawing Sheets

(51) Int. Cl.

| | | |
|---|---|---|
| *A23L 3/00* | (2006.01) | |
| *B08B 9/20* | (2006.01) | |
| *A23C 3/07* | (2006.01) | |
| *A23B 4/015* | (2006.01) | |
| *A23B 4/26* | (2006.01) | |
| *B08B 3/12* | (2006.01) | |
| *A23L 3/30* | (2006.01) | |
| *A61L 2/025* | (2006.01) | |
| *A61L 2/04* | (2006.01) | |
| *B06B 1/12* | (2006.01) | |

(52) U.S. Cl.
CPC ............... *A61L 2/04* (2013.01); *B06B 1/12* (2013.01); *B08B 3/12* (2013.01); *B08B 3/123* (2013.01); *B06B 2201/71* (2013.01)

(58) Field of Classification Search
USPC .............. 422/20, 38, 127–128, 292, 307; 134/25.3, 61, 84; 426/234, 237; 99/451
See application file for complete search history.

(56) References Cited

U.S. PATENT DOCUMENTS

| 6,537,600 | B1 | 3/2003 | Meldrum | |
|---|---|---|---|---|
| 2004/0251773 | A1 | 12/2004 | Manchester et al. | |
| 2005/0061355 | A1 | 3/2005 | Berman et al. | |
| 2012/0027898 | A1* | 2/2012 | Misawa | A23L 3/3508 426/238 |

FOREIGN PATENT DOCUMENTS

| FR | 2918589 | 1/2009 |
|---|---|---|
| WO | 2009/115543 | 9/2009 |

OTHER PUBLICATIONS

GB Search Report dated Feb. 10, 2017 for GB Application No. 1613333.2.
GB Examination Report dated Jul. 3, 2017 for GB Application No. 1613333.2.

\* cited by examiner

DISINFECTION OF FOODSTUFFS

BACKGROUND OF THE INVENTION

This invention relates to methods and apparatus for the sterilisation or disinfection of products such as foodstuffs and more particularly but not solely to meat.

The shelf life of food is substantially shortened due to the presence of micro-organisms in the food, which can cause the food to deteriorate. Not only does shelf life affect the economic viability of food producers but it has a direct effect on public health, since the presence of certain micro-organisms in food can be hazardous if the food is ingested. These problems can be exacerbated if the food is not kept sufficiently refrigerated or is undercooked, since the micro-organisms in the food can multiply rapidly.

In order to overcome the above-mentioned problems, it has been proposed to pasteurise food. However, a disadvantage of pasteurisation is that the process is lengthy and can only be used on certain types of food. Furthermore, the pasteurisation process affects the taste of the food and is costly to perform, since it uses a substantial amount of energy, a great deal of which is discharged into the working environment.

In one known method, the food is packaged in an atmosphere which inhibits the fast reproduction of micro-organisms. One such an approach is to package the food product within a carbon dioxide atmosphere. This has proved to be difficult to control, environmentally unfriendly and expensive to run. It also does not kill pathogenic micro-organisms but instead merely slows down their reproduction rate.

Independent tests have shown that the new invention is particularly good at disinfecting the surface of meat without imparting any taste, change of texture or change of colour.

The micro-organisms which infect meat are particularly difficult to disinfect without changing the organoleptic qualities of the meat, campylobacter on chicken and *E coli* 0157 on beef being particularly difficult to eradicate.

Another feature of meat is that its surface is covered with micro-cracks, fissures and pores which provide protection for the micro-organisms and prevent easy access to disinfectants.

Thermal disinfection processes such as steam or water scalding, for example at 100° C. seriously degrade the product and are not acceptable to either the food manufacturers or the retailers.

Strong chemicals and biocides are not acceptable because they impart objectionable tastes and or smells, and are banned for the processing of chicken in Europe.

UV disinfection although being efficient and fast in killing micro-organisms is unable to thoroughly disinfect meat as it can only kill micro-organisms that are exposed to the UV light; unfortunately a high proportion of the micro-organisms are not exposed but hidden from the UV light, usually by the poor transmissivity of the water as it fouls over time.

The solution to this problem is a process which removes the micro-organisms from the surface and pores of the meat without changing its organoleptic qualities into a medium such as water so that they can then be exposed to some form of disinfection and be deactivated or killed.

Previous work done with ultrasonic wave energy has shown that there is a disinfection effect on micro-organisms due to the implosion effect of collapsing vacuum bubbles caused by the Ultrasonic wave energy and the shear stresses caused by the implosion phenomenon. There is also evidence that this shearing effect causes the formation of free radicals stripped from the water.

Microbiologists have established that the proteins which make up the DNA of microorganisms start to congeal at 55° C.-65° C. and if enough of these proteins congeal quickly then the microorganism dies quickly.

Suitable disinfectors are UV radiation, Ultrasonic wave energy and hot water between 55° C. and 90° C. Preferably the disinfection system is Ultrasonic wave energy and hot water.

Work done with hot water as a disinfector shows that it is a fast efficient disinfector but to some products which are temperature sensitive it can cause unacceptable damage.

Testing carried out on whole chicken has shown that with short treatment times 75° C. is acceptable, 80° C. is marginal and 85° C. is unacceptable. For some microorganisms, short treatment times will not give the required kill rate and increasing the treatment time causes damage to the product, therefore with heat sensitive products this becomes a major problem.

The following invention addresses the aforementioned problem.

SUMMARY OF THE INVENTION

Aspects of the invention are as set out in the independent claims and optional features are set out in the dependent claims. Aspects of the invention may be provided in conjunction with each other and features of one aspect may be applied to other aspects.

DRAWINGS

Embodiments of the disclosure will now be described, by way of example only, with reference to the accompanying drawings, in which.

Figure 7:
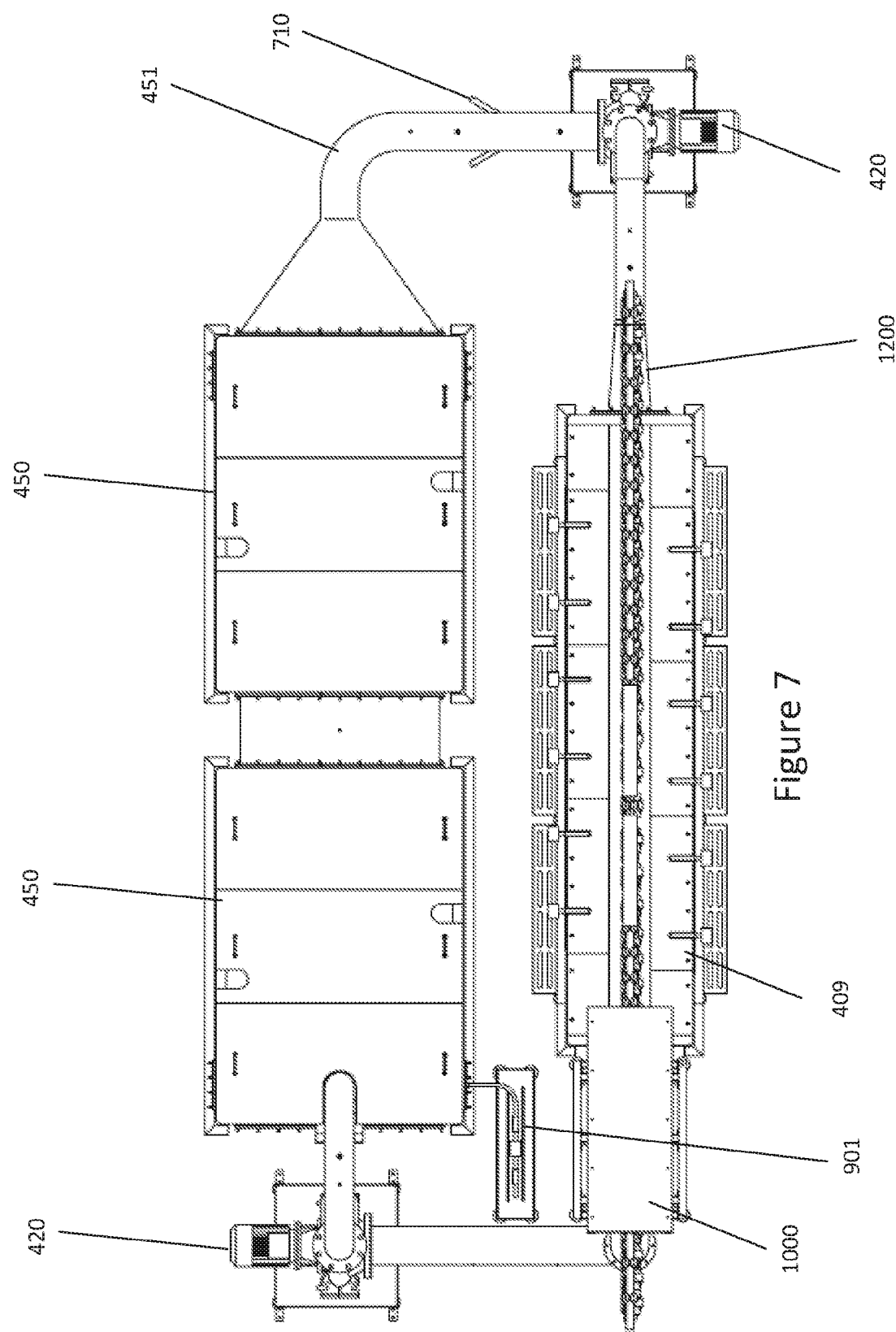
FIG. 7 shows a plan view of another example disinfecting apparatus.
Figure 12C:
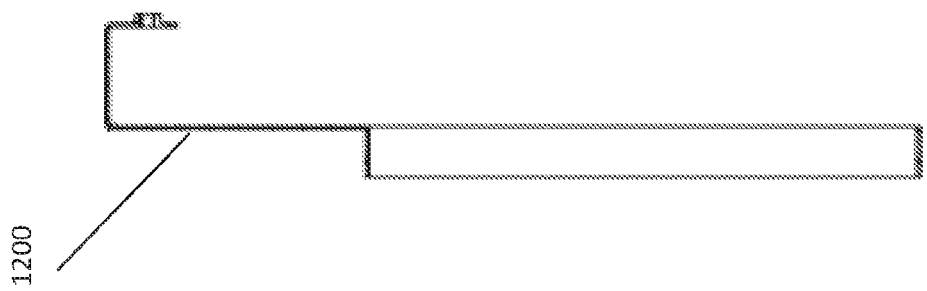
Figure 12B:
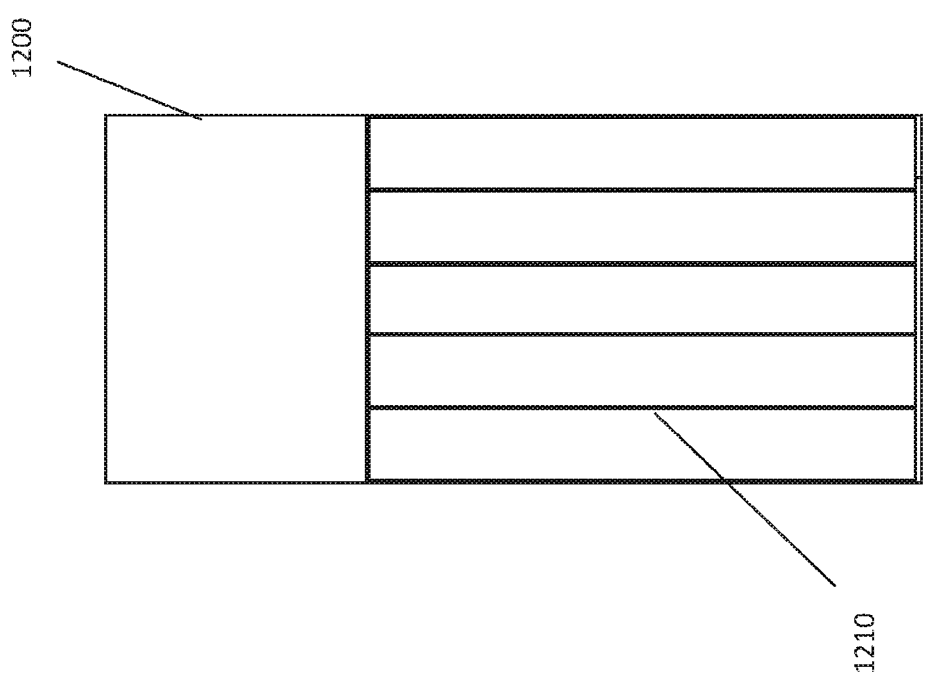
Figure 12A:
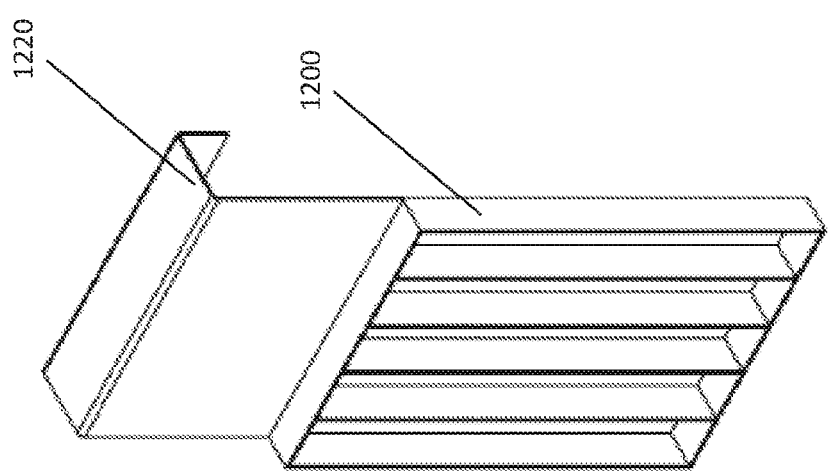
Figure 13:
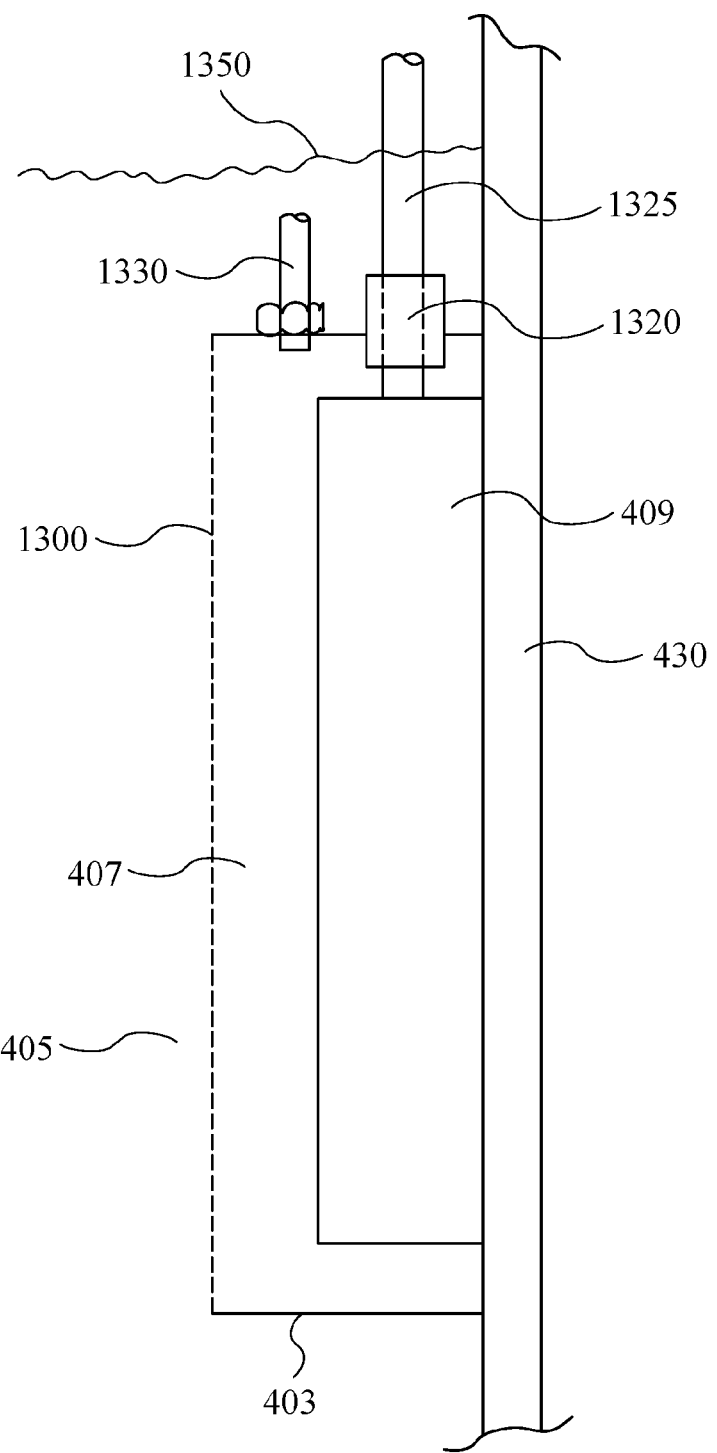

FIGS. 12*a*, 12*b* and 12*c* show perspective, side and end view of a straightener for use with a disinfecting apparatus, such as the disinfecting apparatus of FIG. 7;

FIG. 13 shows a cross-section through a tank of an example disinfecting apparatus, such as the disinfecting apparatus of FIG. 7.

SPECIFIC DESCRIPTION

Tests carried out by the inventor have shown that there is not a single process which satisfactorily disinfects the product rather it has been shown that two synergistic processes working together gives a good disinfection result (up to 4-5 log microorganism reduction). The preferred process comprises ultrasonic wave energy combined with hot water.

Figure 1:
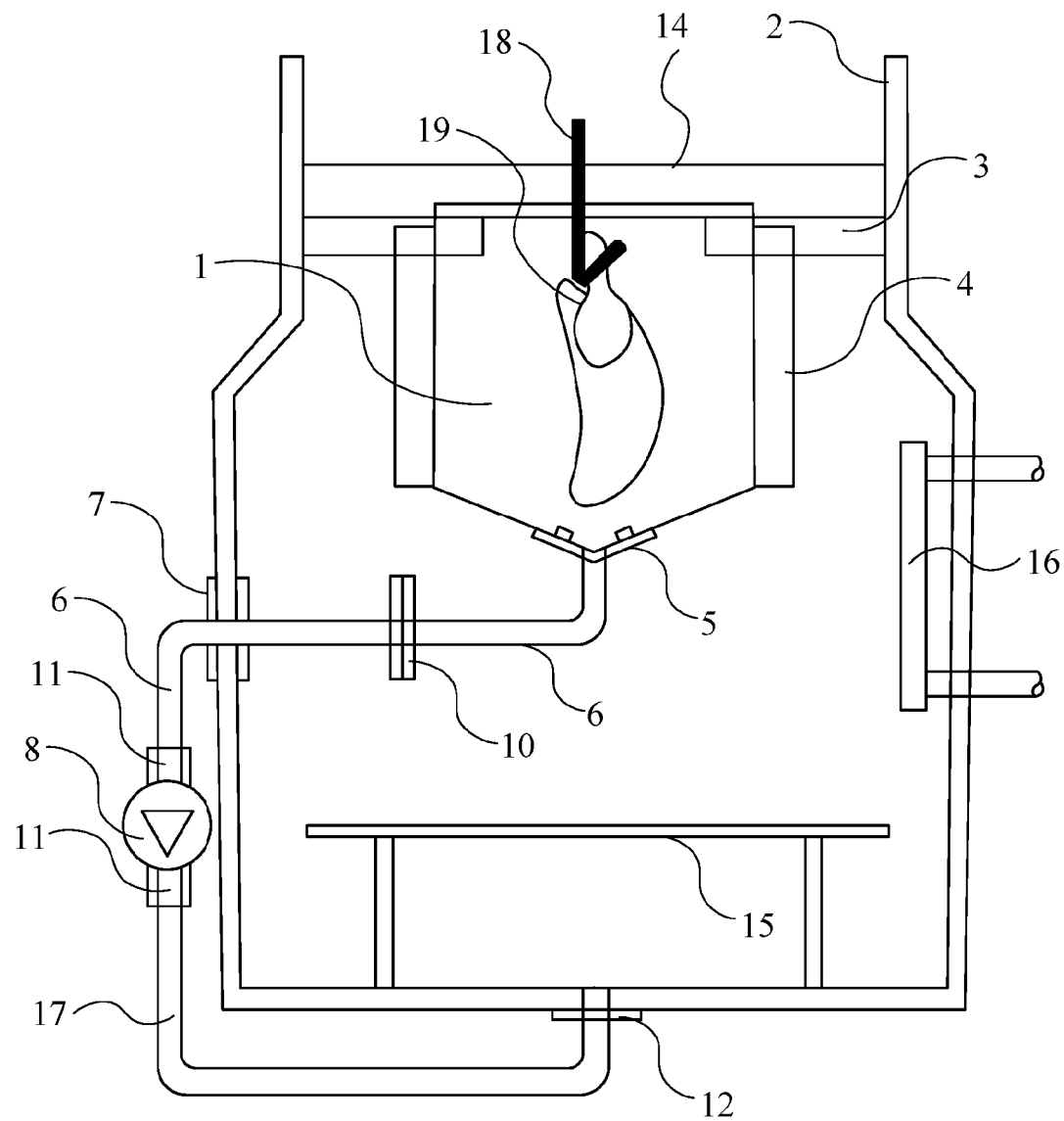
FIG. 1 shows a partial sectional view of an ultrasonic tank supported inside an outer tank.
Figure 2:
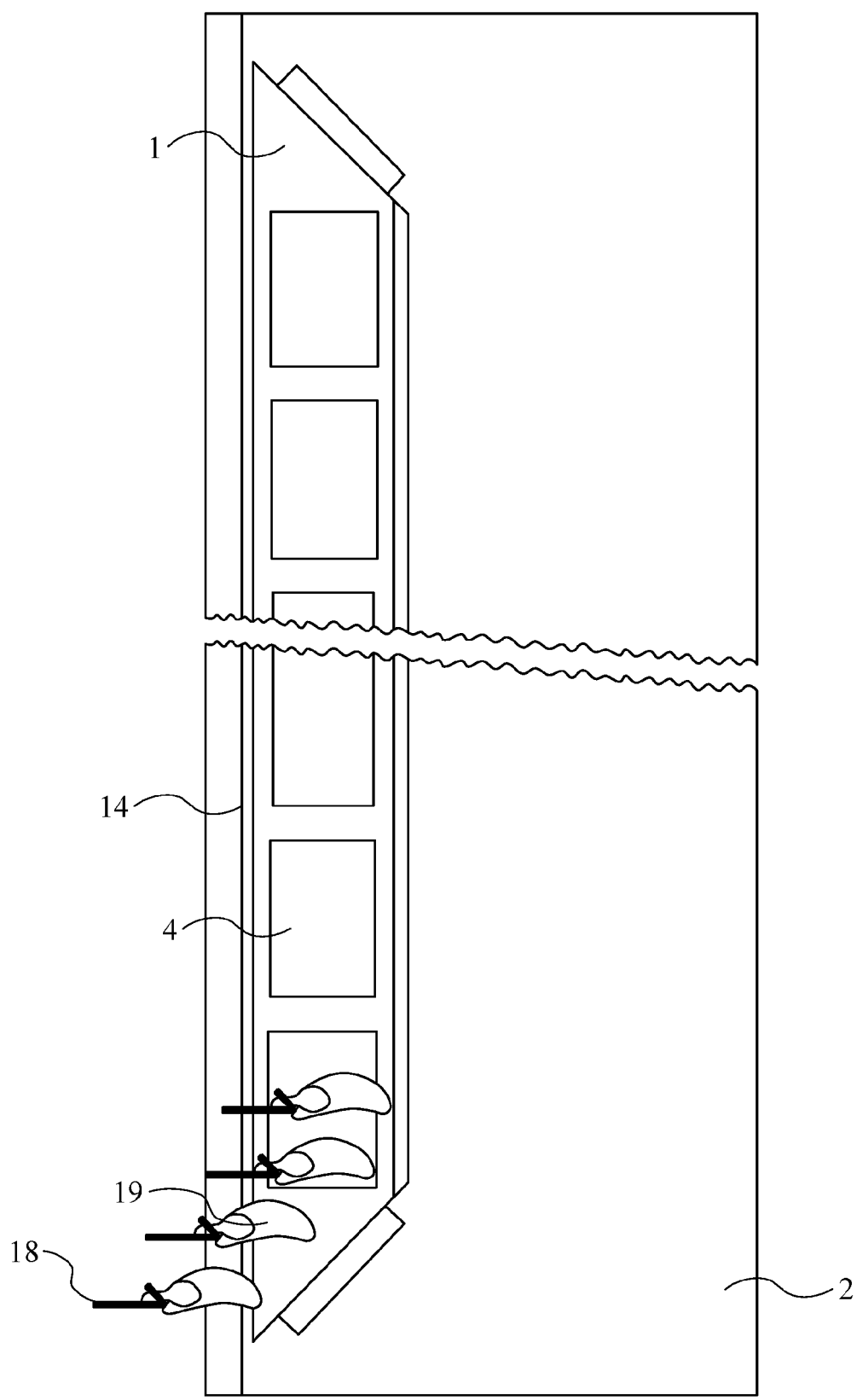
FIG. 2 shows a side view of an ultrasonic tank supported inside an outer tank.

In a first embodiment and with reference to FIGS. 1 & 2—A rectangular inner tank 1 is positioned inside a rectangular outer tank 2 and supported from brackets 3 rigidly attached to the inside wall of the outer tank 2. The inner tank 1 has ultrasonic transducers 4 placed inside the tank to produce ultrasonic wave energy inside the inner tank 1. Preferably the ultrasonic transducers 4 are placed on the walls of the inner tank 1. Preferably the outer tank is heat insulated to minimize heat loss from the outer tank.

When the inner tank 1 is filled with a fluid e.g. a liquid such as water (for example to a level to cover the transducers), and the ultrasonic transducer 4 is driven by an ultrasonic oscillator (not shown) then ultrasonic waves are generated from the ultrasonic transducer 4 which vibrate the fluid at the ultrasonic frequency in the range 20 kHz to 100 kHz; preferably the ultrasonic transducer 4 is of the magnetostriction or quartz crystal or ceramic type capable of developing powers greater than 500 Watts. Preferably the power of the ultrasonic transducer is greater than 1000 Watts.

Attached to the base of the inner tank via a flange 5 is a pipe 6 positioned to convey water from the inner tank 1 through the wall of the outer tank 2 via a watertight flange 7 to the inlet of a pump 8 where it is rigidly attached with watertight fittings 11. One end of pipe 17 is rigidly attached with watertight fittings 11 to the outlet of pump 8 and the other end is rigidly attached with watertight fittings 12 to the base of the outer tank 2 thus a watertight conduit is formed from and through the base of tank 1 through the pump 8 and through the base of the outer tank 2. The pipe 6 is joined by a flange 10 for ease of construction.

When the tanks 1 and 2 are filled with water up to the optimum water level 14 the inner tank is fully submerged and the water is heated either by a heater 16 directly in the tank or indirectly by a heat exchanger 16 system (not fully shown).

The operation of the invention will now be explained with the aid of FIG. 1.

When in operation the steady state conditions are as follows;

The water is at the optimum level 14 and has been heated to the desired temperature by the heater 16. The pump 8 is switched "on" and the ultrasonic transducers 4 are energized.

A conveyor 18 is positioned such that it travels over the inlet end of the inner tank 1 carrying the product 19 to be disinfected through the tank 1 at a depth coinciding with the center of the ultrasonic transducers 4. The product is conveyed through the tank 1 and out at the exit end of the tank 1. With the ultrasonic transducer 4 energized by the ultrasonic power oscillator (not shown) the microbiological contamination on the product 19 is forced off the product due to the ultrasonic wave energy causing a microscopic scrubbing effect on the surface of the product 13. The micro-organisms are forced into the water from the surface as well as from any micro-cracks, fissures and pores on the product 13. The pump forces the water to flow through the tank 1 in a downward flow carrying the microbiological contamination with it. Any clumps of slime may be broken down to individual microorganisms by the ultrasonic wave energy.

The contaminated water is conveyed through the pump 8 and into the outer tank 2 whose water is also at the desired temperature. The contaminated water at this point is moving at a fast forward velocity and makes contact with the baffle plate 15 which slows it down encouraging the contaminated water to stratify, although of course in other examples other types of baffle may be used. If the volume of the inner tank 1 is small in relation to the outer tank 2 then the rate of water flow through the inner tank will be fast but through the outer tank 2 will be much slower.

The contaminated water proceeds through the outer tank 2 and the relatively long time in the hot water kills the microbiological contamination meanwhile the disinfected water at the top of the outer tank keeps the inner tank permanently full and the process cycles continuously. Preferably the outer tank 2 is rigidly fixed to a base frame (not shown) which in turn is rigidly fixed to the floor.

If the treatment meets the acceptable temperature and time requirements for the product in the inner tank and the temperature and time requirements to kill the biological contamination in the outer tank then this invention addresses the aforementioned problem associated with temperature sensitive products.

For products contaminated with micro-organisms which are more resistant to heat and would need a disinfecting water temperature which is higher than the product can stand without unacceptable deterioration, the water temperature in the inner tank 1 must be lower than the water temperature in the outer tank 2. This allows the micro-organisms to be dislodged in acceptable low temperature water then transferred to high temperature water for disinfection.

Figure 3:
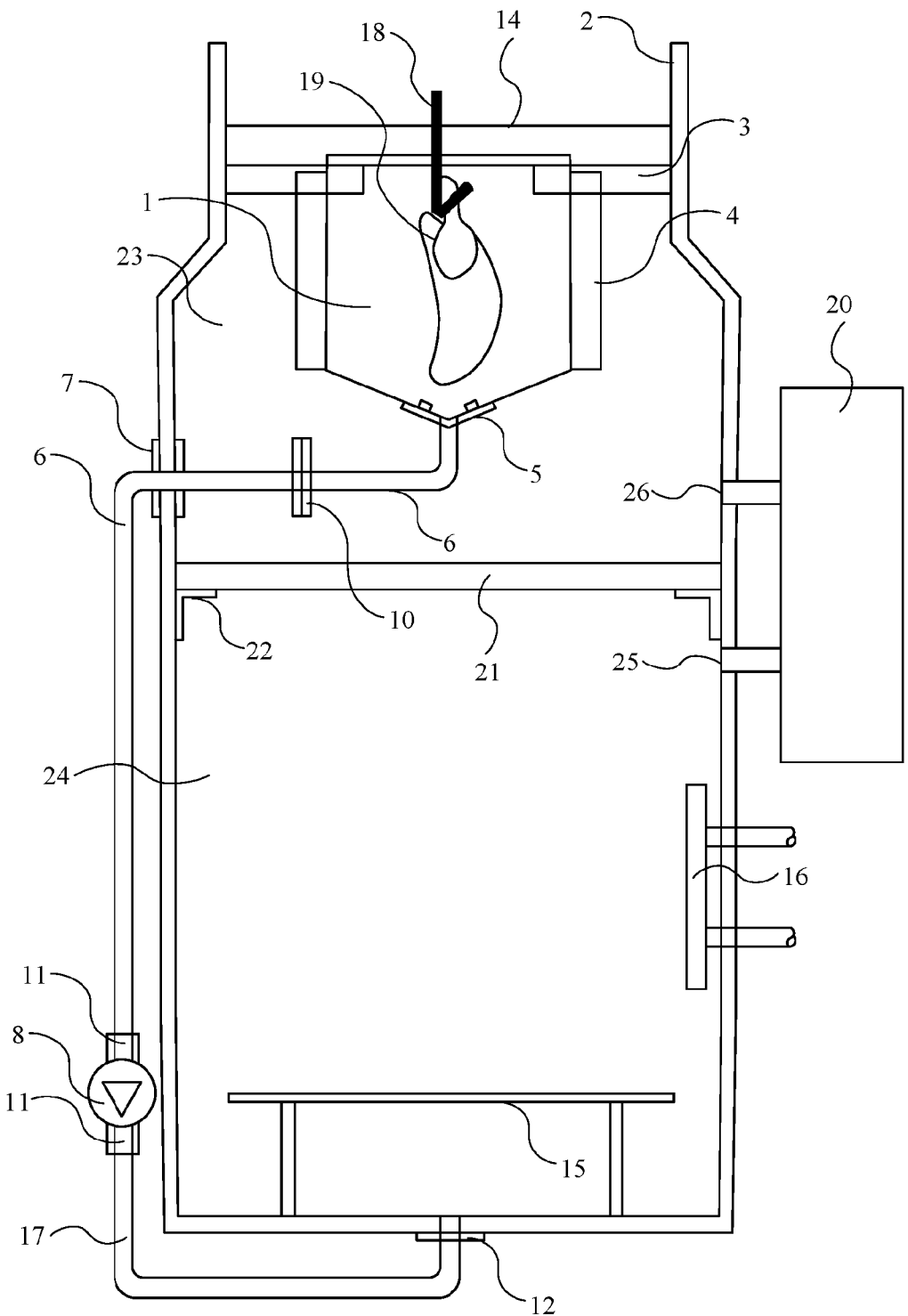
FIG. 3 shows a plan view of ultrasonic tank with submerged heaters, shallow wide tank.

In a second embodiment and referring to FIG. 3—A substantially rectangular inner tank 1 positioned inside a rectangular outer tank 2 and supported from brackets 3 rigidly attached to the inside wall of the outer tank 2. The inner tank 1 has ultrasonic transducers 4 placed inside the tank to produce ultrasonic wave energy inside the inner tank 1. Preferably the ultrasonic transducers 4 are placed on the walls of the inner tank 1. Preferably the outer tank is heat insulated to minimize heat loss.

When the inner tank 1 is filled with a fluid e.g. water and the ultrasonic transducer 4 is driven by an ultrasonic power oscillator (not shown) then ultrasonic waves are generated from the ultrasonic transducer 4 which vibrate the fluid at the ultrasonic frequency in the range 20 kHz to 100 kHz; preferably the ultrasonic transducer 4 is of the magnetostriction or quartz crystal or ceramic type capable of developing powers greater than 500 Watts. Preferably the power of the ultrasonic transducer is greater than 1000 Watts.

Attached to the base of the inner tank via a flange 5 is a pipe 6 positioned to convey water from the inner tank 1 through the wall of the outer tank 2 via a watertight flange 7 to the inlet of a pump 8 where it is rigidly attached with water tight fittings 11. One end of pipe 17 is rigidly attached with water tight fittings 11 to the outlet of pump 8 and the other end is rigidly attached with water tight fittings 12 to the base of the outer tank 2 thus a watertight conduit is formed from and through the base of tank 1 through the pump 8 and through the base of the outer tank 2. The pipe 6 is joined by a flange 10 for ease of construction. When the inner tank 1 and outer tank 2 are filled with water up to the optimum water level 14 the inner tank is fully submerged.

The outer tank 2 is partitioned by a thermally insulated partition 21 rigidly fixed to the inside walls of the outer tank 2 by brackets 22 effectively making the outer tank 2 into two tanks an upper tank 23 and a lower tank 24. The water in the lower tank 24 is heated either by a heater 16 directly in the tank or indirectly by a heat exchanger 16 system (not fully shown).

A flow through chiller 20 is positioned with its input port 25 rigidly fixed with watertight fittings to and through the wall of the lower tank 24 and its output port 26 rigidly fixed with watertight fittings to and through the wall of the upper tank 23 so that any water flowing through the lower tank 24 will automatically flow through the chiller 20 and into the upper tank 23 and be cooled from its original disinfection temperature to a temperature which the product can be processed without sustaining unacceptable damage.

When the inner tank 1 and outer tank 2 are filled with water up to the optimum water level 14 the inner tank is fully submerged and the water in the lower tank 2 is heated either by a heater 16 directly in the tank or indirectly by a heat exchanger 16 system (not fully shown) to produce the disinfection temperature. When the disinfection temperature is reached the chiller 20 and the pump 8 are switched "on" and the system starts to circulate providing the correct process temperature in the upper tank 23 and the correct disinfection temperature in the lower tank 24.

The operation of the invention will now be explained with the aid of FIG. 3.

When in operation the steady state conditions are as follows;

The water is at the optimum level 14 and has been heated to the desired temperature in the upper tank 23 via the chiller 20 and the desired disinfection temperature in the lower tank 24 by the heater 16. The chiller 20 and the pump 8 are switched "on" and the ultrasonic transducers 4 are energized.

A conveyor 18 is positioned such that it travels over the inlet end of the inner tank 1 carrying the product 19 to be disinfected through the inner tank 1 at a depth coinciding with the center of the ultrasonic transducers 4. The product is conveyed through the tank 1 and out at the exit end of the tank 1. With the ultrasonic transducer 4 energized by the ultrasonic power oscillator (not shown) the microbiological contamination on the product 19 is forced off the product due to the ultrasonic wave energy causing a microscopic scrubbing effect on the surface of the product 13. The micro-organisms are forced into the water from the surface as well as from any micro-cracks, fissures and pores on the product 13. The pump 8 forces the water to flow through the tank 1 in a downward flow carrying the microbiological contamination with it.

The contaminated water is conveyed through the pump 8 and into the lower tank 24 whose water is at the desired disinfection temperature. The contaminated water at this point is moving at a fast forward velocity and makes contact with the baffle plate 15 which slows it down encouraging the contaminated water to stratify. If the volume of the inner tank 1 is small in relationship to the outer tank 2 then the rate of water flow through the inner tank will be fast but through the outer tank 2 will be much slower.

The contaminated water proceeds through the lower tank 24 and the relatively long time in the hot water kills the microbiological contamination meanwhile the disinfected water at the top of the lower tank 24 flows into the inlet 25 of the chiller 20, through the chiller 20 to be cooled to the required processing temperature for the inner tank 1. Then the cooled and disinfected water flows out of the outlet 26 of the chiller 20 into the upper tank 23 and hence into the inner tank 1. The water level 14 keeps the inner tank 1 permanently full and the process cycles continuously. Preferably the outer tank 2 is rigidly fixed to a base frame (not shown) which in turn is rigidly fixed to the floor.

This invention allows heat sensitive products to be processed by splitting the process into two distinct synergistic techniques. A technique for removing micro-organism contamination from a product 19, using ultrasonic wave energy, and into water at a temperature which does not cause unacceptable damage to the product 19 and quickly move the contaminated water into water at a high temperature to kill the micro-organism contamination, then deliver the disinfected water back into the inner tank 1 at the correct processing temperature.

There are several other example configurations that can be employed to achieve this solution;

1) The outer tank could be split into two distinct tanks with the chiller straddled between the two tanks.
2) The chiller 20 could be remote or the outer tank 2 could be split into three separate tanks with the chiller being the middle tank.
3) The heater 16 or heat exchanger 16 could be remote.
4) The inner tank can be positioned outside of the outer tank, for example separate to the outer tank, and the fluid pumped to it (for example horizontally), instead of being submerged in the outer tank.

These are but a few possible configurations and those skilled in the art will find different Configurations, nevertheless this should not detract from the scope of the invention as defined by the appended claims.

Preferably a water filter process is added to the tanks to remove oil, fat and general debris from the water to keep it clear. Several products are commercially available for this purpose and those skilled in the art of water treatment will be able to provide suitable schemes.

The whole process may be automatically controlled by a PLC to provide consistently high disinfection results.

In some examples the lower or outer tank 24 described above may be a reservoir. The volume of the outer tank or reservoir may be greater than that of the upper or inner tank 23. Accordingly, an aspect of the disclosure provides an apparatus for disinfecting a product, the apparatus comprising a tank arranged to provide ultrasonic energy to the product via a liquid such as water for forcing microorganisms off the product and into the liquid, and a reservoir arranged to receive and heat liquid transferred from the tank into the reservoir. The temperature of the liquid in the reservoir is selected to disinfect the microorganisms forced off the products into the liquid.

The apparatus may be configured to heat the liquid to the same temperature as the tank, or to a temperature hotter than that of the tank. For example, the apparatus may be configured to heat the liquid in the reservoir to a selected temperature, for example to a range of between 70° C. and 90° C., for example to at least 70° C., or to at least 75° C. The reservoir may comprise at least one of a heater and a heat exchanger for heating the liquid to the selected temperature. The tank and/or reservoir may be insulated to inhibit heat loss from the liquid. In some examples, the reservoir may comprise a plurality of tanks.

The volume of the reservoir may be larger than that of the tank so that the liquid remains in the reservoir for longer than in the tank, for example so that the liquid remains in the tank for less than 5 s, and in the reservoir for at least 30 s.

The dwell time and temperature of the liquid in the reservoir may be selected to disinfect the microorganisms forced off the products into the liquid, for example so that the liquid remains in the reservoir at a temperature of at least 75° C. for at least 30 s. The reservoir may comprise at least one baffle arranged to slow the flow of liquid through the reservoir (and hence increase the dwell time) for encouraging the liquid to stratify.

In some examples, the tank is inside the reservoir. In other examples the tank may be outside the reservoir. For example, the apparatus may be arranged to transfer liquid horizontally from the tank to the reservoir. The apparatus and/or reservoir may be configured to recirculate the liquid to the tank. The apparatus may further comprise a flow through chiller for cooling the recirculated liquid and/or a filter for filtering the recirculated liquid.

As shown in the Figures, in some examples the apparatus comprises a conveyor 18 for carrying the product 19 through the tank. The apparatus may also comprise an ultrasonic power oscillator coupled to the at least one ultrasonic transducer for driving the at least one ultrasonic transducer. The conveyor may carry the product through the liquid at a depth coinciding with the centre of the at least one ultrasonic transducer.

Another aspect of the disclosure is an apparatus for disinfecting products, for example foodstuffs such as meat, for example as shown in FIGS. 4A to 6. The apparatus 400 comprises a tank 401 for holding a liquid for receiving microorganisms from the products 19. The tank 401 comprises a barrier 403 separating two regions of liquid, the two regions comprising a first region 405 and a second region 407. The first region 405 is arranged to provide an open channel 404 (in the example shown in the form of a U-shaped trough and is open-topped) for the liquid to flow through the tank 401 to enable a product 19 to be carried into, along, and out of a flowpath through the channel 404. The second region 407 is configured to hold liquid adjacent to at least one ultrasonic transducer 409 for providing ultrasonic energy to the product via the liquid in the second region 407 and through the barrier 403 for forcing microorganisms off the product 900 and into the liquid in the first region 405.

Figure 6:
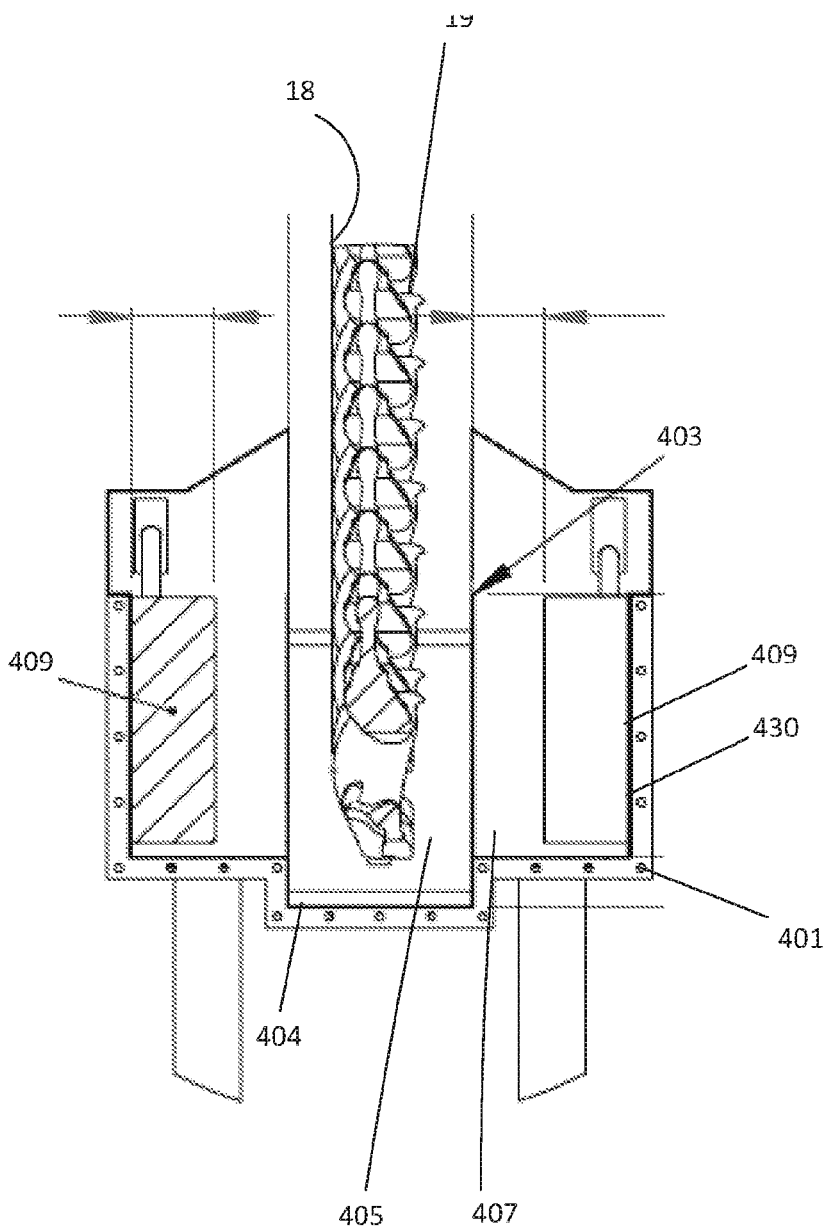
FIG. 6 shows an end cross-section of a tank of the disinfecting apparatus of FIG. 4A

An example apparatus is shown in FIGS. 4A to 6. The apparatus 400 comprises an elongate tank 401. As shown in FIG. 6, the elongate tank 401 is substantially rectangular in cross-section and comprises two barriers 403 extending substantially the whole length of the tank 401 and separating two regions 405, 407 of liquid in the tank 401, although in other examples only one barrier 403 may be used. The barriers 403 define two sides of a channel 404 providing a flowpath for product 19 through the tank 401. The channel 404 corresponds to the first region 405, with the second region 407 being either side (or in some examples only to one side of) the channel 404.

In the example shown in FIG. 6 the channel 404 is in the middle of the tank 401 and is deeper than the region 407 to either side of the channel 404, although in other examples the channel 404 may have the same depth as the rest of the tank 401. For example, the channel 404 may be 377 mm deep whereas the rest of the tank may be 317 mm deep. The length of the channel 404 may be 2865 mm. The width of the channel 404 may be 220 mm, whereas the width of the tank may be 654 mm.

The channel 404 is open (in the examples shown the tank 401 forms a trough that is open-topped), although the tank 401 may comprise a lid 415 covering a portion, for example a central portion, of the channel 404. The lid 415 is arranged to have openings for a conveyor 18 to carry product 19 into, through and out of the channel 404.

The barrier 403 is coupled to a wall of the tank 401 along its bottom edge. In some examples, the coupling and the barrier 403 are watertight, for example the barrier 403 may be made from an impermeable material such as glass or metal (such as stainless steel), so that the two regions 405, 407 of liquid are kept separate. In other examples, the barrier 403 may be permeable, for example the barrier 403 may comprise pores that are impermeable below a selected pressure (such as less than 1 bar, less than 2 bar) and permeable above a selected pressure (such as more than 1 bar, more than 2 bar, more than 3 bar). In some examples, the liquid held in the second region 407 is different to the liquid held in the first region 405. For example, the liquid held in second region 407 may be deionised water while the liquid held in the first region 405 may be normal tap water. The barrier 403 may be arranged to keep the liquid adjacent to the ultrasonic transducers 409 in the second region 407 clean; for example, the barrier 403 may be configured to allow liquid to flow from the second region 407 to the first region 405 but not from the first region 405 to the second region 407.

In some examples the barrier 403 comprises a material having an acoustic impedance greater than that of water. For example, the barrier may comprise a material having an acoustic impedance of at least $12 \times 10^6$ kg/m$^2$sec, for example at least $35 \times 10^6$ kg/m$^2$sec. The barrier may be 3-6 mm thick, for example the barrier may be 18 to 22 gauge stainless steel.

The tank 401 comprises a plurality of ultrasonic transducers 409 arranged along the channel 404, although it will be understood that in some examples only one ultrasonic transducer 409 is used. In some examples, twelve ultrasonic transducers 409 are used. The plurality of ultrasonic transducers 409 may be arranged either side of the channel 404, for example mirroring each other, or along only one side of the channel 404. In the examples shown, the plurality of ultrasonic transducers 409 are evenly spaced along the length of the channel 404 and in the example shown are hung over an edge of the tank 401 so that they can easily be removed for cleaning and so that the edge of the tank can have a smooth surface free of joins which may further aid cleaning of the inside of the tank 401. In other examples, however, it will be understood that the transducers 409 may be fixed in another way, for example by bonding the transducers 409 to an outside surface of the material forming the inner wall of the tank 401.

The plurality of ultrasonic transducers 409 may be staggered or offset from each other. For example, as shown in FIG. 7, the plurality of ultrasonic transducers 409 are hung over an edge of the tank 401 and may be arranged so that the ultrasonic transducer 409 on one side of the channel 404 overlaps with an ultrasonic transducer 409 on the opposite side of the channel 404, for example so that an ultrasonic transducer 409 on one side of the channel 404 overlaps with an ultrasonic transducer 409 on the opposite side of the channel 404 by at least 50% of its width. The plurality of ultrasonic transducers 409 may extend substantially the whole height of the tank 401 and/or channel 404. The plurality of ultrasonic transducers 409 may be phase linked and/or synchronised, for example synchronised in frequency. For example, the ultrasonic transducers 409 may be configured to operate at several frequencies in the range of 50 to 85 kHz, some of which are more effective than others. In some examples the ultrasonic transducers 409 may have an asynchronous sweep frequency which may be frequency modulated to a pattern of frequencies. The ultrasonic transducers 409 may each be coupled to a respective generator and amplifier (not shown). The ultrasonic transducers 409 may each operate at 1 kW.

Each ultrasonic transducer 409 is coupled to a wall 430 of the tank 401 inside the tank 401. In this way, each ultrasonic transducer 409 defines a boundary of the liquid in the second region 407. For example, each ultrasonic transducer 409 may form a wall of the tank 401.

The barrier 403 may comprise a respective window for each ultrasonic transducer 409 for transmitting ultrasonic pressure waves from the second region 407 to the first region 405. The size of each window may be selected based on the size of the corresponding ultrasonic transducer 409. Each respective window may be acoustically insulated from the other windows, for example by a strip of insulating material such as rubber. The distance between a window in the barrier 403 and the corresponding ultrasonic transducer 409 may be greater than the wavelength of ultrasonic pressure waves produced by the ultrasonic transducer. For example, the distance between the at least one window and the ultrasonic transducer 409 may be greater than 35 mm, for example greater than 50 mm, preferably 63 mm.

The apparatus 400 also comprises a second tank or reservoir 450 arranged to receive and heat liquid transferred from the (first) tank 401 comprising the barrier 403 separating the two regions 405, 407. In the example shown in FIGS. 4A to 6, the second tank or reservoir 450 comprises two separate vessels in fluid communication, although in other examples the second tank or reservoir 450 may only comprise one vessel.

The second tank or reservoir 450 is coupled to the (first) tank 401 by a pipe 451. In the example shown in FIGS. 4A to 6, the tank 401 and reservoir 450 are at the same height (for example they are mounted on the same surface), although it will be understood that in other examples the tank 401 and reservoir 450 may be a different heights, or for example the tank 401 may be inside the reservoir 450, similar to the examples shown in FIGS. 1 to 3 and described above.

As with the examples shown in FIGS. 1 to 3, the reservoir 450 comprises a heater 16. The heater 16, for example, may comprise submerged heating elements in the reservoir 450. The heater 16 may also comprise a temperature sensor. The reservoir 450 also comprises a baffle or series of baffles such as the baffles 15 described above. The volume of the second tank or reservoir 450 is greater than that of the (first) tank 401. For example, the volume of the (first) tank 401 may be 339 litres and the volume of the reservoir 1447 litres, although if the reservoir comprise two vessels, the total volume (i.e. capacity) of the reservoir may be double this. In some examples, the reservoir 450 may also comprise a filter and additionally or alternatively a chiller for cooling the liquid.

Coupled to the tank 401 is a flow provider 420. The flow provider 420 may comprise a pump, such as an impeller pump. In the example shown, the flow provider 420 is in-line with the pipe 451 coupling the reservoir to the tank 401. As noted above, the apparatus 400 also comprises a conveyor 18 for carrying the product 19 through the liquid in the channel 404. The conveyor 18 may have baskets or hooks for carrying and dipping the product 19 in the liquid in the channel 404.

Figure 4A:
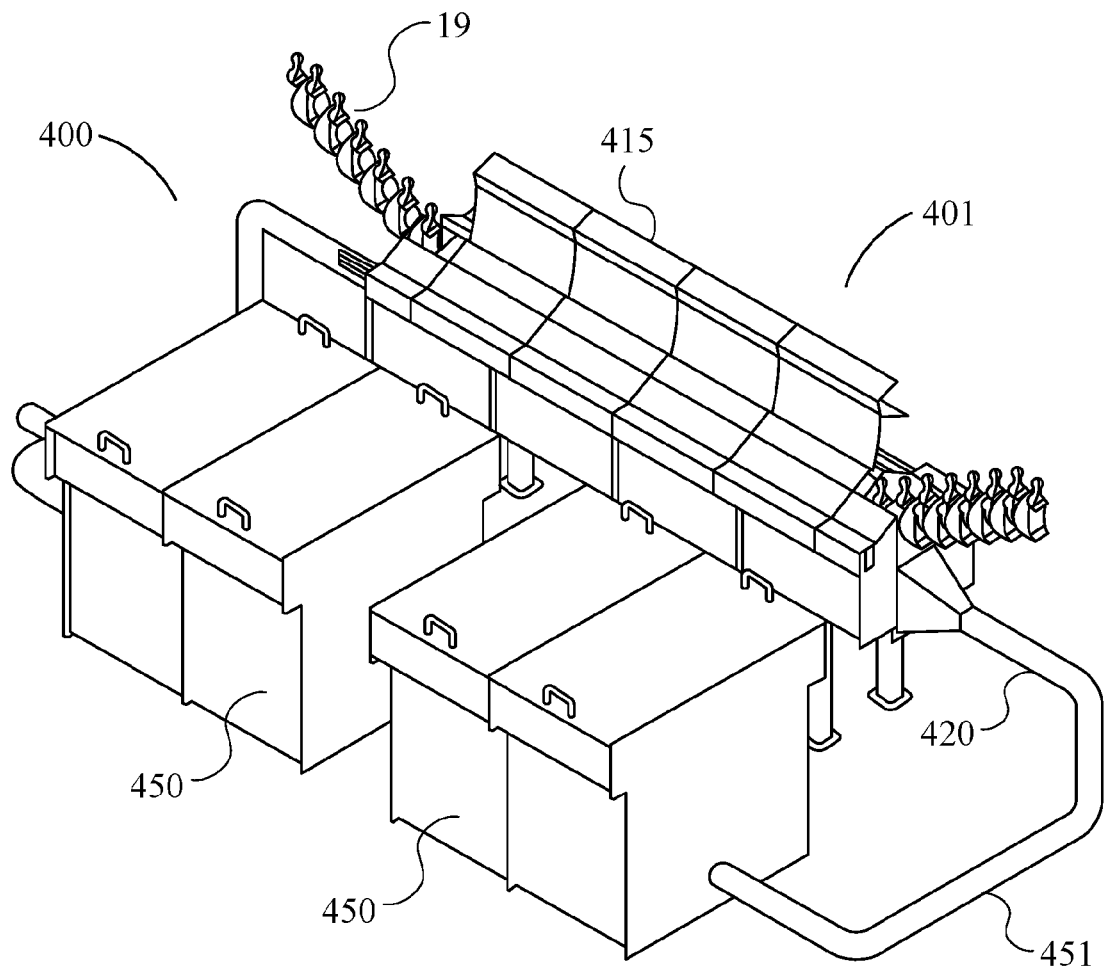
FIG. 4A shows a perspective view of an example disinfecting apparatus.
Figure 4B:
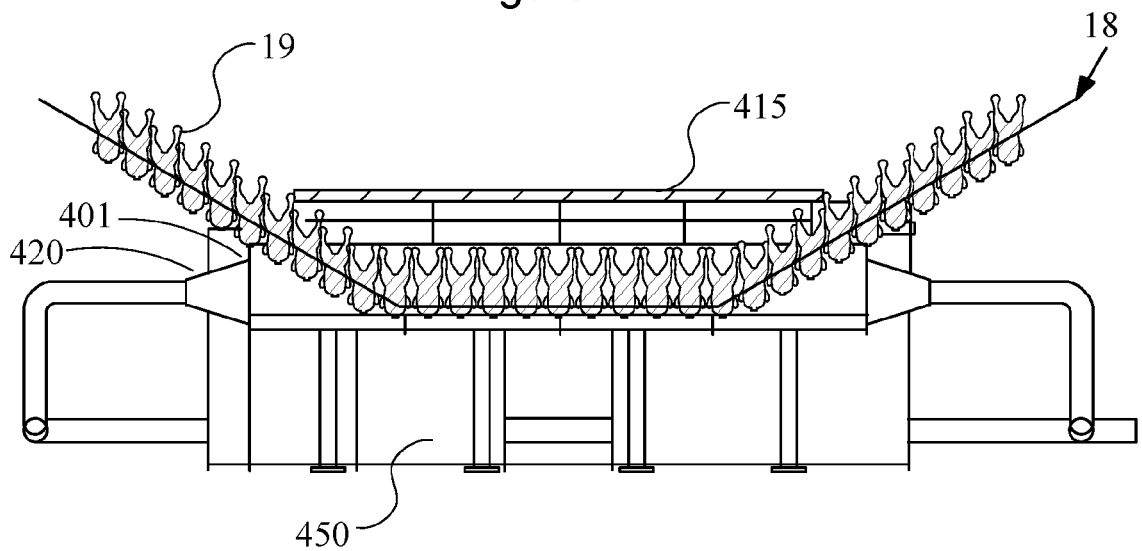
FIG. 4B shows a side cross-section of the disinfecting apparatus of FIG. 4A.
Figure 5A:
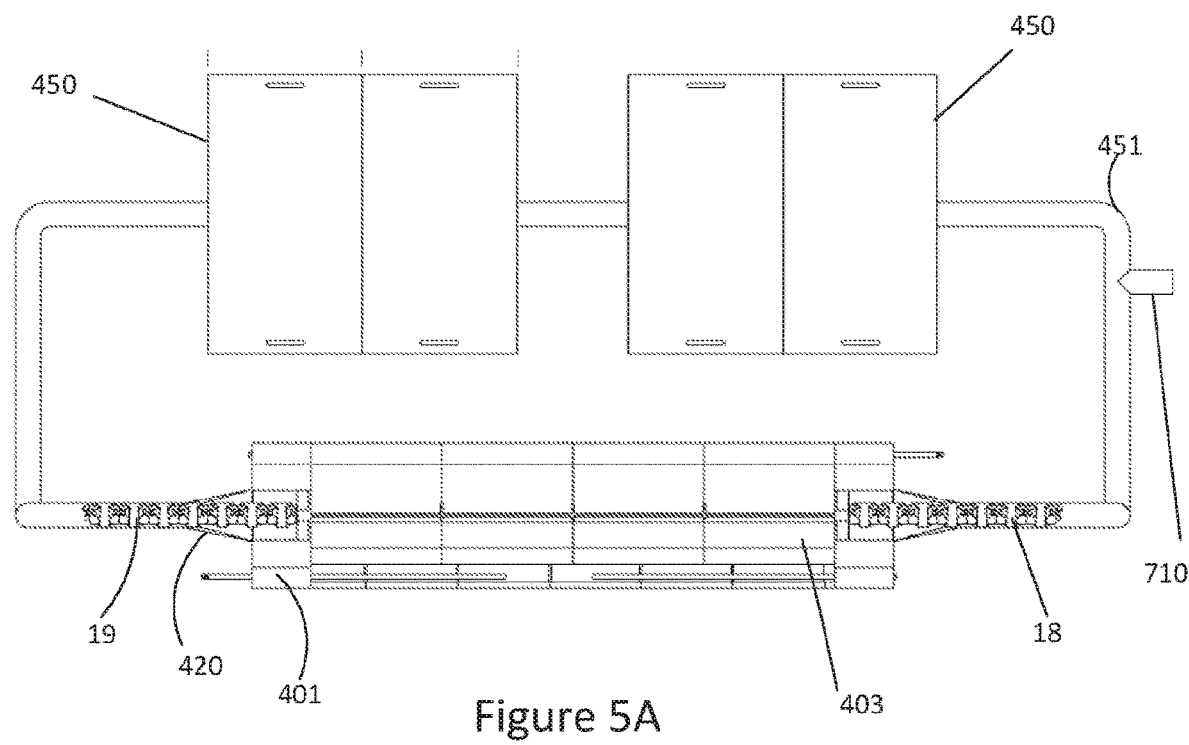
FIG. 5A shows a plan view of the disinfecting apparatus of FIG. 4A.
Figure 5B:
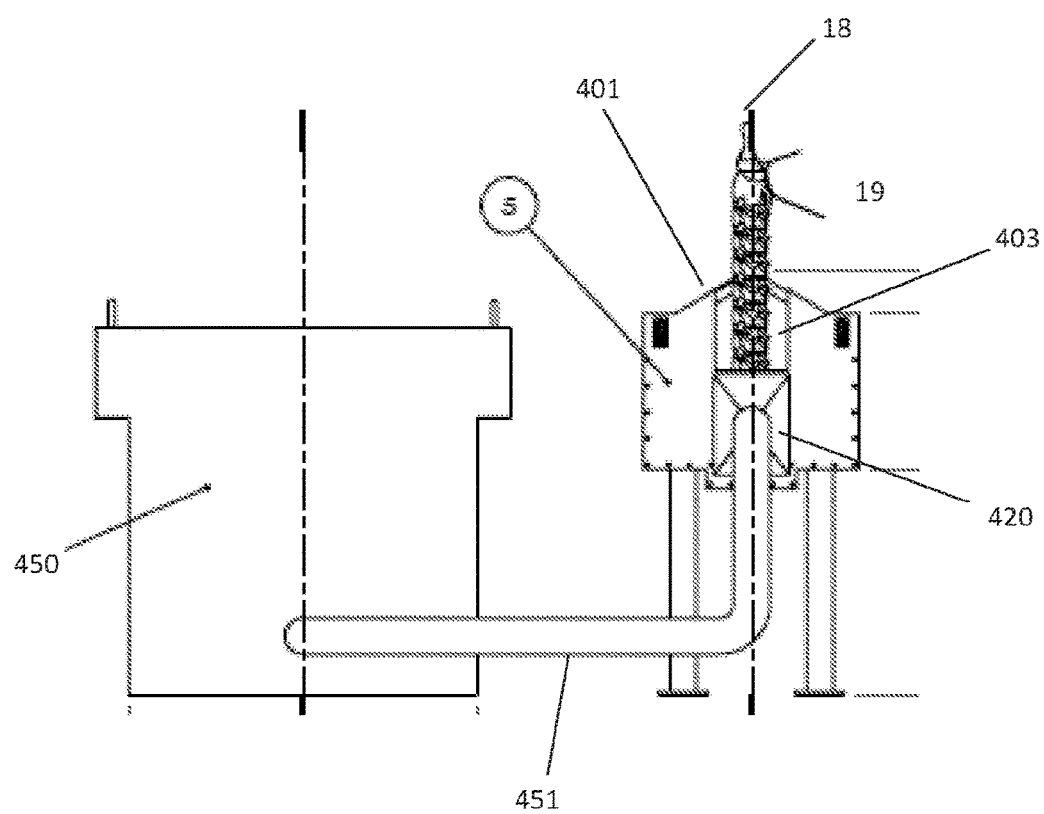
FIG. 5B shows an end view of the disinfecting apparatus of FIG. 4A.

The ultrasonic transducers 409 are operable to provide ultrasonic energy to the product 19 through the liquid in the second region 407, through the barrier 403, and through the liquid in the first region 405, to a product 19 held in the flowpath in the channel 404. The channel 404 and lid 415 are arranged so that the conveyor 18 carrying the product 19 can carry the product into, through and out of the liquid in the channel 404, as shown in FIGS. 4A and 4B. The conveyor 18 may carry the product 19 along the entire length of the channel 404 or only along a portion of the length of the channel 404. The position of the ultrasonic transducers 409 may be selected to provide ultrasonic energy to the centre of the product 19 when the product is submerged in the liquid of the channel 404.

If the barrier 403 comprises a window, the window is configured to transmit ultrasonic energy from liquid on one side of the barrier 403 to liquid on the other side of the barrier 403. The degree of ultrasonic energy provided to the product by the ultrasonic transducers 409 is selected to damage, dislodge or force microorganisms from the surface of the product 19 into the liquid.

The flow of product 19 through the channel 404 creates a flowpath that draws liquid along with the product 19 in the channel 404. This flow of product 19 can create turbulence in the liquid. The flow provider 420 coupled to the tank 401 is arranged to provide a flow of liquid through the channel 404 in the first region 405 at a velocity selected based on that of the conveyor 18 carrying the product through the liquid. For example, the flow provider 420 may be configured to adjust the flow rate of liquid through the channel 404 to match the velocity (in terms of both speed and direction) of the product 19 being carried by the conveyor 18. Matching the velocity of the liquid through the channel 404 to that of the product 19 may help to reduce turbulence (and thereby the creation of undesirable bubbles in the liquid) and hence increase the efficacy of the transmission of ultrasonic energy to the product 19 from the ultrasonic transducers 409. In some examples, the flow provider 420 may have an output with a cross-sectional area that is selected or adjusted to provide a substantially laminar flow through the channel at the velocity selected based on that of the conveyor 18. The flow provider 420 may also be operable to control the flow of liquid from the tank 401 to the reservoir 450 and thereby recirculate liquid through the apparatus 400.

The tank 401 may be configured to hold the liquid in the second region 407 (adjacent to the ultrasonic transducers 409) at a relatively stationary velocity. Because the liquid adjacent to the ultrasonic transducers 409 is relatively stationary, this again may increase the efficacy of the transmission of ultrasonic energy to the product 19.

Operation of the ultrasonic transducers 409, the flow provider 420 and the conveyor 18 may be controlled by a controller comprising a programmable logic circuit, PLC. The PLC may also be configured to control the temperature of the liquid (for example by controlling operation of a heater 16 or a chiller 20 as described above). The PLC may form an open loop system. In some examples, the PLC may be configured to receive signals, for example from a temperature sensor for detecting the temperature of the liquid in the reservoir 450, or a flow meter for detecting the velocity of the liquid in the tank 401, and adjusting the outputs for the heater 16 or flow provider 420 as appropriate. The contact time of the product 19 with the liquid in the channel 404 of the tank 401 and/or the flow rate of liquid through the channel 404 of the tank 401 may be selected based on the temperature of the liquid in the tank 401, for example so that the contract time is reduced as a function of increasing temperature. For example, the speed of the conveyor 18 and/or the flow rate of liquid through the channel 404 may be selected to achieve the desired contact time determined based on the temperature of liquid in the tank 401 and the length of the channel 404 in the tank 401.

The baffles 15 in the reservoir 450 are arranged to slow the flow of liquid through the reservoir 450, thereby encouraging the liquid and any debris carried by the liquid to stratify. For example, the baffles 15 may be arranged to provide a labyrinth-like flow path through the reservoir 450 and/or extend the flow path for liquid through the reservoir 450, for example the baffles 15 may provide a serpentine flow path through the reservoir 450. The baffles 15 may be configured to cause the flow path to perform a series of U-turns or 180° turns. The heater 16 is operable to heat the liquid in the reservoir to a selected temperature, for example a selected disinfection temperature in a range of 70° C. to 90° C., such as at least 70° C., at least 75° C., for example at least 80° C., for example at least 85° C., and/or may use an optional temperature sensor as a feedback mechanism to operate at the selected temperature. The temperature of the liquid in the reservoir 450 may be higher than that of the temperature of the liquid in the tank 401.

The reservoir 450 is configured to treat (for example disinfect) the liquid being circulated through the apparatus 400. The flow provider 420, the volume of the reservoir 450 and the selection and arrangement of baffles 15 may be configured to adjust the dwell time of fluid in the reservoir (the amount of time fluid flowing through the reservoir remains in the reservoir) and thereby the treatment time of the fluid in the reservoir 450. For example, the volume of the reservoir 450 may be selected based on the flow rate of liquid in the channel 404 and the speed of the conveyor 18 carrying the product 19 through the channel 404 so that at that flow rate a desired dwell time is desired. For example, if a longer dwell time in the reservoir 450 at a selected flow rate is desired, the volume of the reservoir 450 may be increased to increase the dwell time of the liquid in the reservoir 450.

In use, the product 19 is carried by the conveyor 18 into, through and out of the channel 404 of the tank 401. The speed of the conveyor 18 and/or the length of the channel 404 (and hence the dwell time of the product in the liquid of the channel 404) may be adjusted based on the ultrasonic energy applied to the product and/or the temperature of the liquid in the channel 404, but may be at least 5 seconds, for example at least 6.5 seconds. The conveyor 18 may carry the product at a speed of, for example, 0.5 m per second, resulting in 12,000 products being processed per hour. The flow rate of liquid through the tank 401 and reservoir 450 may be at least 22 L/s, and in some examples may be at least 44 L/s.

The ultrasonic transducers 409 provide energy to the product via the second 407 and first 405 regions (and through the barrier 403) which act to dislodge and scrub the product 19 to force microorganisms off the product 19 and into the liquid in the channel 404. The liquid in the channel 404 is driven along by the flow provider 420 so that liquid is recirculated from the tank 401, through the pipe 451 to the reservoir 450. As the liquid enters the reservoir 450, it is slowed by the baffles 15 and the volume of liquid in the reservoir 450. As the liquid slows it begins to stratify. The heater 16 acts to heat the liquid to the selected temperature (for example a selected disinfection temperature such as at least 75° C. or at least 80° C. or at least 85° C.). The arrangement of the baffles 15, the volume of the reservoir 450 and the flow rate provided by the flow provider 420 is selected to control the dwell time of liquid in the reservoir. The dwell time and the temperature of the liquid in the reservoir are selected to disinfect the liquid and to kill any microorganisms forced off the product 19 into the liquid, for example as described in other aspects of the disclosure. For example the dwell time may be selected to be at least 30 seconds, and in some examples may be at least 60 seconds. However it will be understood that the dwell time may be selected based on the temperature of the liquid in the reservoir 450, for example so that the dwell time is reduced (for example linearly) as a function of increasing temperature.

Once the liquid passes through the reservoir 450, before it passes to the flow provider 420 it may be filtered by an optional filter, and/or it may be cooled by a chiller (such as chiller 20 described above) so that the temperature of the liquid does not damage or degrade the product 19.

In examples where the reservoir 450 comprises two vessels, each vessel may be configured to have a different temperature and/or dwell time. For example, each vessel may act so as to serve a different purpose. For example, one vessel may have a high temperature to kill microorganisms (such as, for example, at least 80° C.), and the other vessel may have a lower temperature (such as, for example, less than 80° C., for example equal to and/or less than 75° C.) and/or may act to cool the liquid to a temperature acceptable for recirculating to the tank 401 (such as, for example, equal to and/or less than 75° C.) and for exposure to the product 19. Additionally or alternatively, each vessel may have a different size and/or volume.

In some examples the temperature of the liquid in the tank 401 is the same as the temperature of the liquid in the reservoir 450, although in other examples the temperature of the liquid in the reservoir 450 is equal to, or hotter than, the liquid in the tank 401. For example, the temperature of the liquid in the tank 401 may be at least 70° C., or at least 75° C., and the temperature in the reservoir 450 higher than this, for example at least 80° C. or at least 85° C. In some examples the liquid in the tank 401 and the liquid in the reservoir 450 may both be within a selected temperature range, for example 70° C. to 90° C., and the temperature of the liquid in the tank 401 may be lower within that selected range than the temperature of the liquid in the reservoir 450. In some examples, cooler liquid may be fed into the system to help regulate the temperature of the liquid in the tank 401. For example, as shown in FIG. 7, cool liquid may be fed into pipe 451, for example via a flow provider 710 such as a pump, from an external source of liquid. The cooler liquid may be fed into the pipe 451 between the reservoir 450 and the tank 401, such that liquid being recirculated from the reservoir 450 back into the tank 401 is cooled by the incoming cool liquid. The cool liquid may also help to replace any liquid lost from the system due to carryover on the product 19 as it exits the tank 401.

In some examples, the tank 400 may also comprise a run-off weir along the top edge of the channel 404. The reservoir 450 may also comprise a run-off weir along its top edge. The run-off weirs may be configured to collect debris/oils/fats forced off the product 19 by the ultrasonic energy. For example, the run-off weir may be configured to collect any debris that has stratified and floated to the top of the liquid in the reservoir 450 and thereby remove it from the liquid Apparatuses described herein may be configured to disinfect foodstuffs, for example meat such as chicken or beef, or nuts.

Although the examples described above in relation to FIGS. 4 to 6 comprise one flow provider 420 coupled to the tank 401, in some examples there may be more than one flow provider 420, for example as shown in FIG. 7. For example, as shown in FIG. 7, there may be two independent flow providers 420, each independently controllable, for example by the PLC. For example, there may be a flow provider 420 arranged to control the flowrate of liquid through the tank 401, and another flow provider 420 arranged to control the flowrate of liquid through the reservoir 450 and/or a respective flow provider 420 for each vessel forming the reservoir 450. In this way, the flowrate of liquid through the apparatus can be better controlled to achieve optimal disinfection.

Figure 9:
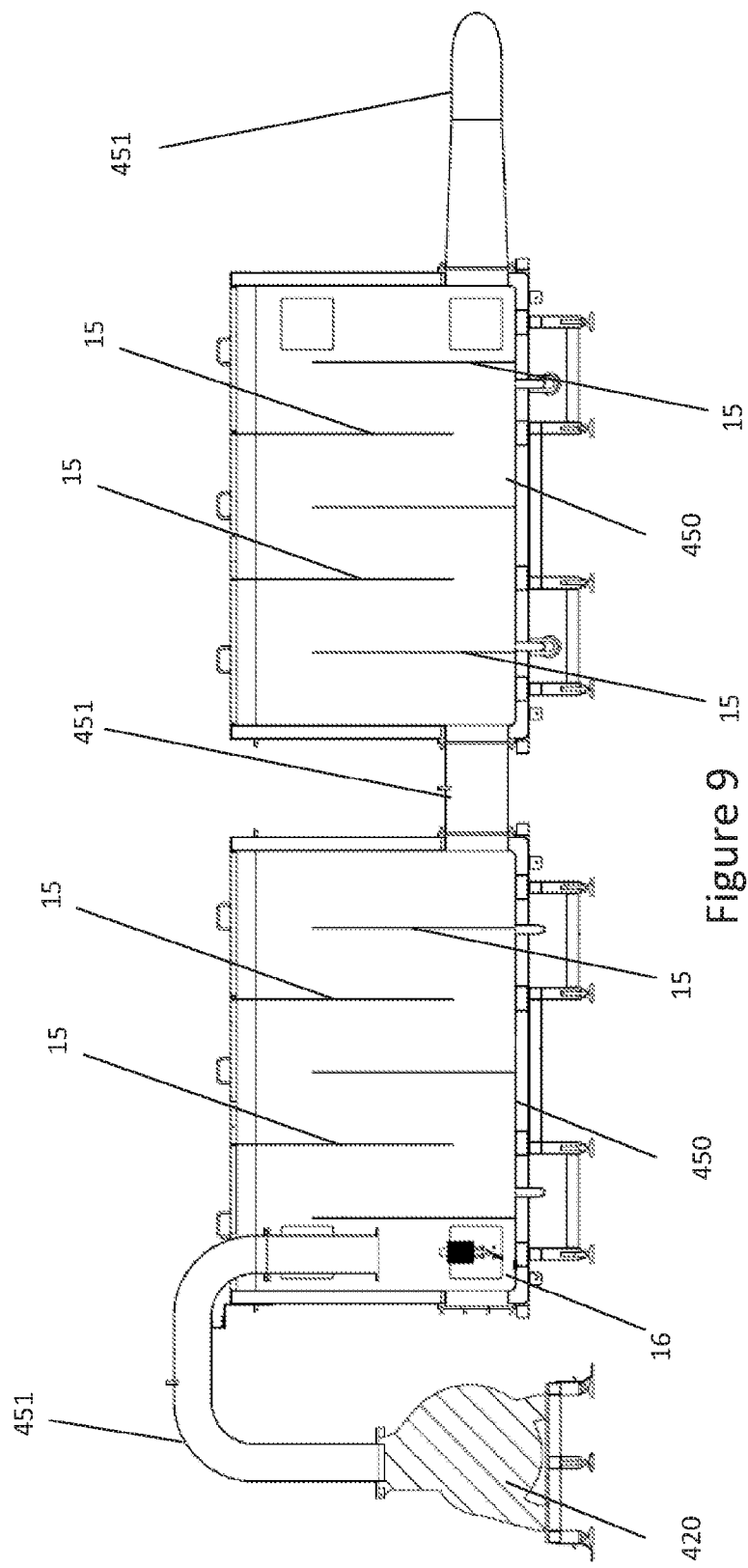
FIG. 9 shows a cross-section through the reservoir of an example disinfecting apparatus, such as the disinfecting apparatus of FIG. 7.

In some examples, the series of U-turns or 180° turns forming the baffles 15 may be formed by a plurality of overflow and underflow weirs as shown in FIG. 9, such that the liquid flows over and under each of the baffles 15 in a serpentine or labyrinth-like pattern as it passes through the reservoir 450. The pipe 451 may be arranged to feed liquid into the reservoir 450 from above, for example as shown in FIG. 9 the pipe 451 is arranged to form a U-shape up and over the edge of the reservoir 450 so that the pipe 451 extends into the reservoir 450 so that it is submerged below the waterline of liquid in the reservoir 450 and so that liquid is fed into the reservoir 450 near the bottom of the reservoir 450 proximal to the heater 16. In this way, liquid entering the reservoir 450 is displaced upwards (as opposed to being sprayed) over the first baffle 15 thereby reducing turbulence in the reservoir.

In some examples, such as the example shown in FIG. 9, the heater 16 in the reservoir 450 comprises a plurality of nozzles for injecting steam into the liquid in the reservoir 450. The heater 16 may be located along a bottom surface of the reservoir 450, for example before the first baffle 15, so that incoming liquid comes into immediate contact with the heater 16 thus improving sterilization. For example, steam may be generated by a steam generator 901 coupled to the heater 16 via an inlet pipe, and the steam may be injected into the liquid in the reservoir 450 via the inlet pipe and the nozzles to control the temperature of the liquid in the reservoir 450. In some examples the bubble size of the steam being injected into the liquid in the reservoir 450 can be controlled (for example by controlling the nozzle size and/or the steam production/flow rate) for example to control turbulence in the reservoir 450.

Figure 10:
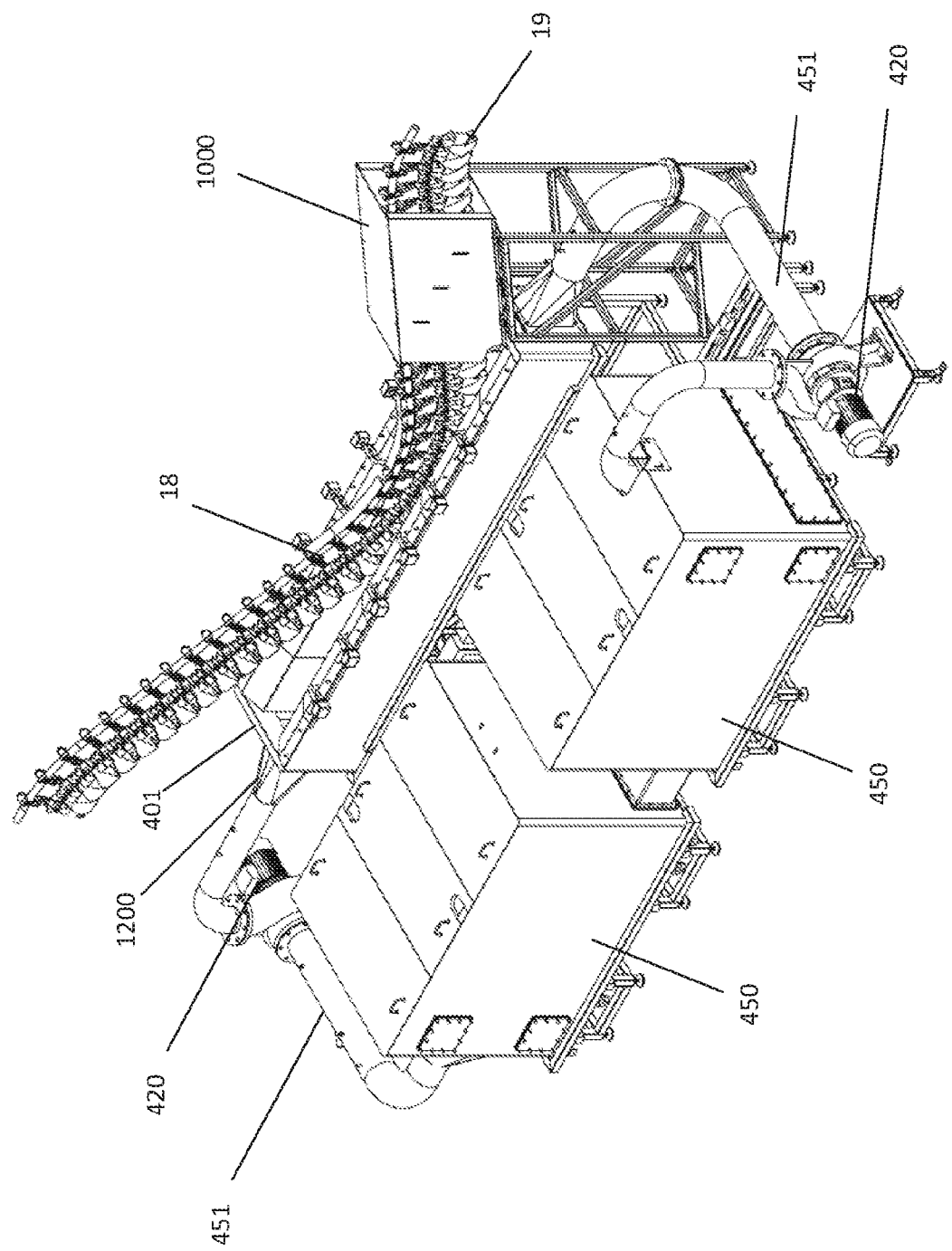
FIG. 10 shows a perspective view of an example disinfecting apparatus, such as the disinfecting apparatus of FIG. 7.

In some examples the apparatus 400 may further comprise a spray wash for rinsing product 19 exiting the channel 404 in the tank 401, for example, as shown in FIG. 10. For example, the apparatus 400 may comprise a rinse hood 1000 comprising nozzle or a plurality/array of nozzles to spray liquid onto the product 19 as it is lifted out of the channel 404 of the tank 401 by the conveyor 18. Liquid may be fed to the nozzles at a pressure of at least 2 bar to achieve effective rinsing of the product 19. The rinse hood 1000 may be configured to follow the course of the conveyor 18, for example so that the rinse hood 1000 provides an enclosure to the conveyor 18 open at either end to allow the passage of product 19 carried by the conveyor 18 through the rinse hood 1000. The nozzles of the rinse hood 1000 may be angled so that liquid is sprayed onto a product 19 that is higher on the conveyor 18 before dripping onto a product 19 that is behind on the conveyor 18, such that products 19 that are further out of the tank 401 are rinsed with fresher liquid. The liquid sprayed onto the product 19 may also help to replace any loss of liquid from the channel 404 due to carryover by the product 19.

Figure 11:
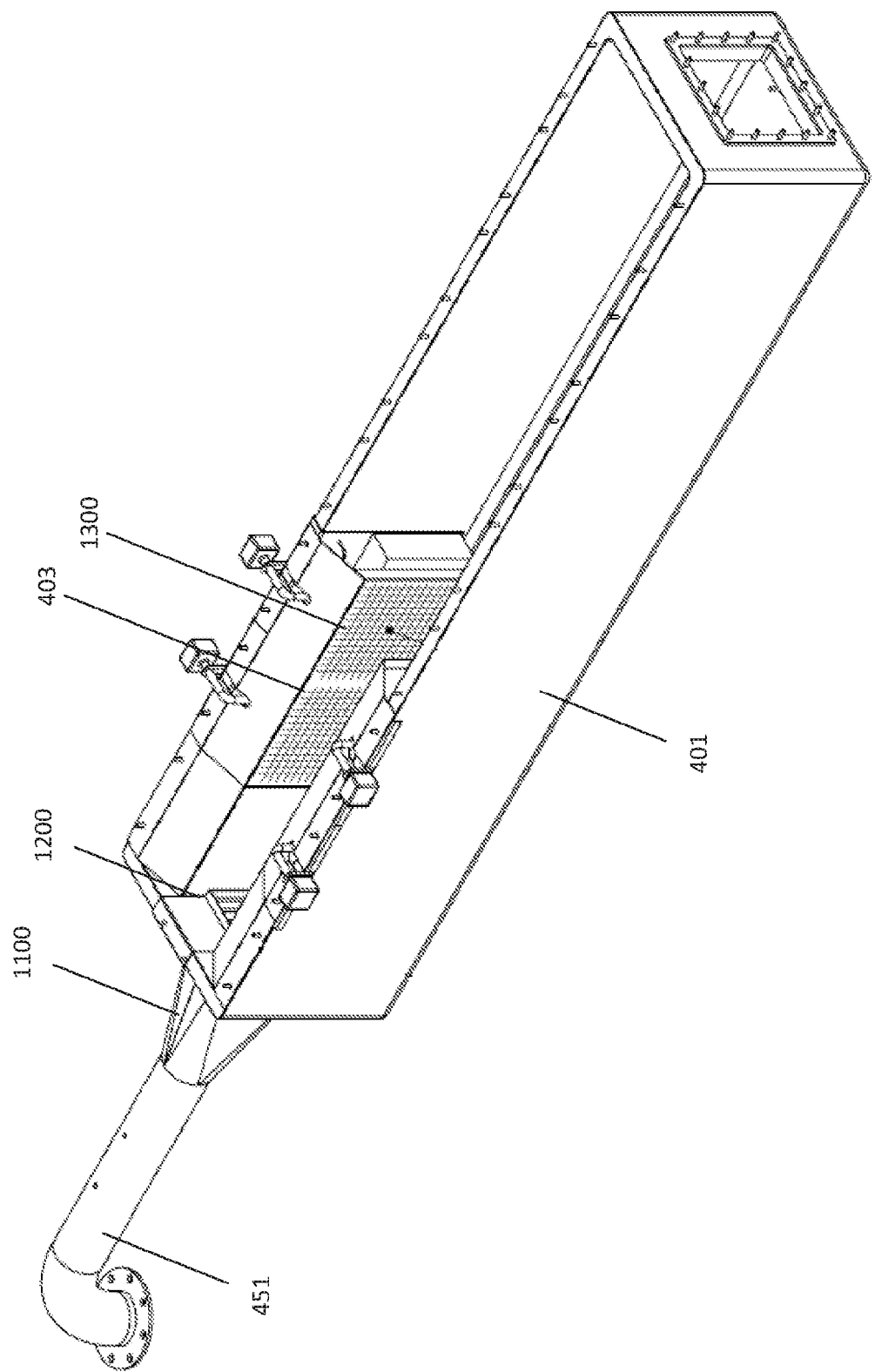
FIG. 11 shows a perspective view of a tank of an example disinfecting apparatus, such as the disinfecting apparatus of FIG. 7.

In some examples the connection between the pipe 451 feeding the tank 401 and/or the reservoir 450 may be shaped to help produce a laminar flow in the tank 401 and reservoir 451 respectively. For example, as shown in FIG. 11, the pipe 451 comprises a nozzle 1100 angled in a conical shape, for example angled at between 10 and 30 degrees, for example 20 degrees, for providing a laminar flow of liquid in the tank 401 and/or reservoir 450. In some examples a mesh may further be placed over the end of the nozzle, for example to help produce a laminar flow of liquid in the channel 440 of the tank 401.

In some examples, a straightener 1200 may be used to further improve the passage of liquid flowing into the tank 401 and help provide a laminar flow in the channel 404 of the tank 401. For example, as shown in FIGS. 11 and 12a, 12b and 12c, a straightener 1200 may be placed over and/or coupled to an inlet to the tank 401 to "straighten" the flow of liquid into the channel 404 of the tank 401. For example, the straightener 1200 may be hung over an edge of the tank 401 by a hook 1220 and placed over an outlet of the flow provider 420, or if present, over a nozzle 1200 of the pipe 451 feeding the tank 401. The straightener 1200 comprises a series of parallel bars or fins 1210 to help guide the flow of liquid therethrough.

As described above, the barrier 403 separates the first region 405 (comprising the channel 404) from the second region 407 of the tank 401. The location of the barrier 403 may be selected so that the channel 404 is only just wider than the width of the product being carried therethrough. Providing a barrier 403 separating the first region 405 from the second region 407 may help to reduce turbulence in the channel 404 as it may help to provide a more uniform boundary to the sides of the channel 404. Also as noted above, in some examples, the barrier 403 may comprise windows. Additionally or alternatively, the barrier 403 may comprise perforations to aid the transmission of ultrasonic energy therethrough. For example, as shown in FIG. 11, the barrier 403 may comprise a plurality of small perforations 1300. For example, the perforations may be at least 3 mm$^2$ and the barrier 403 may be formed from 2-3 mm thick steel, such as 10-14 gauge (SWG) stainless steel, although thinner materials may be used for the barrier, such as 18 gauge (SWG) stainless steel which is approximately 1.2 mm thick. Of course, it will be understood that other materials for the barrier 403 may be used, such as glass. The material the barrier 403 may be fabricated from may be selected based on its acoustic properties such as its acoustic impedance. For example, the material the barrier 403 is made from may be selected to closely match the acoustic impedance of the liquid in the channel 404 of the tank 401, for example to match that of water. The number of perforations 1300 in the barrier 403 may be selected to provide a ratio of open space in the barrier 403 of at least 60%, for example at least 70%. Providing a ratio of open space in the barrier 403 in this range may help improve the power transmission of ultrasonic energy to the product 19.

Figure 8:
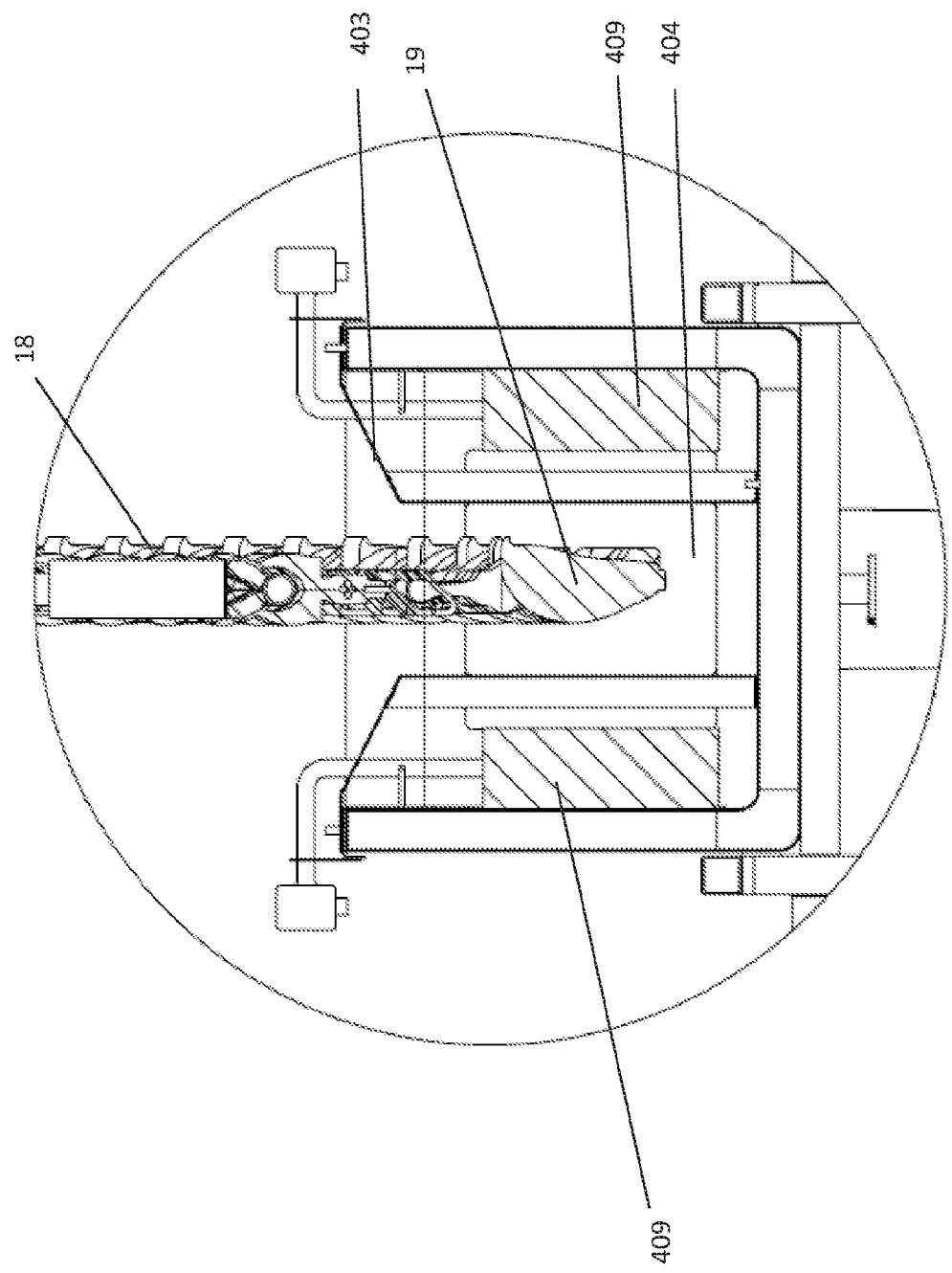
FIG. 8 shows a cross-section of an example tank of a disinfecting apparatus, such as the disinfecting apparatus of FIG. 7.

In some examples, such as the example shown in FIG. 8, the barrier 403 is arranged to provide an enclosure for each ultrasonic transducers 409 or for an array of ultrasonic transducers 409 arranged along a wall of the tank 401. For example, the barrier 403 may be watertight or may inhibit the passage of liquid therein to provide an enclosure. For example the barrier 403 may be coupled to a base of the tank 401 and an inner wall of the tank 401 to enclose the ultrasonic transducer 409.

FIG. 13 shows another example of a barrier 403 for separating a first region 405 from a second region 407 in the tank 401. In the example shown, the ultrasonic transducer 409 is coupled to a wall 430 of the tank 401. The barrier 403 encircles the ultrasonic transducer 409 and comprises three faces. A first face is parallel to a wall 430 of the tank 401 and the other two faces are perpendicular to the wall 430 of the tank 401. The barrier 403 is coupled to the wall 430 of the tank 401 below the waterline 1350 of liquid in the tank 401 to form an enclosure for the ultrasonic transducer 409. The enclosure forms a cavity for liquid to form the second region 407 adjacent to the ultrasonic transducer 409.

The ultrasonic transducer 409 is coupled to a wiring conduit 1325, for example coupling the ultrasonic transducer 409 to the PLC. The wiring conduit 1325 extends out of the tank 401 past the waterline 1350 of liquid in the tank 401, and comprises a watertight seal 1320 to help inhibit the ingress/egress of liquid through a wall of the barrier 403.

The ultrasonic transducer 409 comprises a longitudinal axis parallel to the wall 430 of the tank 401. The barrier 403 comprises a plurality of perforations 1300 on a face parallel to the longitudinal axis of the transducer 409 and parallel to the wall 430 of the tank 401. The size of the perforations 1300 may be selected to aid the transmission of ultrasonic energy from the ultrasonic transducer 409, through the second region 407, through the barrier 403 and into the first region 405, for example as described above.

Providing a barrier 403 that forms an enclosure for the ultrasonic transducer 409 and the second region 407 may help inhibit the creation of turbulence in front of the ultrasonic transducer 407, for example it may help inhibit the creation of turbulence in the second region 407. If turbulence is created in a region outside the enclosure, for example in front of the perforations 1300 of the barrier 403 in the first region 405, it is inhibited from entering the enclosure and thereby the second region 407. This in turn helps to inhibit turbulence from reaching the ultrasonic transducer 409 and may improve the transmission of ultrasonic energy through the liquid.

In the example shown in FIG. 13, the barrier 403 is arranged to inhibit the inlet of liquid into the enclosure formed by the barrier 403. To this extent, in addition to the watertight seal 1320 around the wiring conduit 1325, the barrier 403 also comprises a pressurized liquid inlet 1330. The pressurized water inlet 1330 is arranged to supply liquid to the region enclosed by the barrier 403 (i.e. the second region 407) and thereby create a positive pressure in the second region 407, thereby holding the liquid in the second region 407 at a higher pressure than the liquid in the first region 405. Due to the positive pressure, a small amount of liquid may flow out of the perforations 1300 thereby creating a fluid barrier in front of the barrier 403 and between the perforated wall of the barrier 403 and liquid flowing in the channel 404/first region 405, which will encourage the flow of liquid in front of the barrier 403 to shear past the enclosure formed by the barrier 403. This may help to provide a laminar flow in the channel 404 and this aid the transmission of ultrasonic energy to a product 19 being carried through the channel 404.

In some examples the barrier 403 may further comprise at least one perforation in a bottom wall and/or a top wall to assist filling and draining of the enclosure formed by the barrier 403.

Without wishing to be bound by theory, the present inventors hypothesize that the mode of action of disinfection may be due to the ultrasonic energy waves produced by the ultrasonic transducers 409 disrupting or destroying mucous membranes holding pathogens to the product 19, and may cause damage to pathogen cell walls. In addition, the ultrasonic energy waves may shake the pathogens from the product 19, and force the pathogens/microorganisms off the product 19 and into the liquid. The ultrasonic energy waves may cause complete cell wall rupture and/or pathogens may be consumed in small vacuum bubbles created by the ultrasonic energy waves. The ultrasonic energy waves may also act to cause oxidative destruction of organic materials, for example they may create hydroxyl radicals and/or hydrogen peroxide in the liquid. If the product 19 is a foodstuff such as chicken, the ultrasonic energy waves may create cavitation bubbles in the cavity of the chicken and/or inside the feather follicles, thus aiding in the extraction and removal of pathogens from the potentially inaccessible hair follicle regions of the bird.

Furthermore, without wishing to be bound by theory, in examples where the flow provider is arranged to flow liquid through the channel 404 of the tank 401 in the same direction as the conveyor 18 carrying the product 19 through the channel 404, the product 19 may undergo an initial thermal shock (for example if the product 19 is chilled before it is carried into the liquid in the channel 404) before a small envelope of liquid immediately surrounding the product 19 reaches a thermal equilibrium with the product 19. If the product 19 is a foodstuff, this may help inhibit unwanted heating or cooking of the product 19 as it is carried through the channel 404.

For example, the product 19 may travel through the liquid in the channel 404 in a 'thermal packet' whereby the product 19 and the surrounding liquid (such as hot water) are moved together through the process tank 401. This may be termed a coincident flow.

For example if the product 19 is chilled before it is carried into the liquid in the channel 404, conveying the product 19 through the tank 401 in the same direction as the liquid flowing through the channel 404 may minimize heat damage to the product 19 where the temperature of the liquid is higher than that which the product 19 would normally withstand without being damaged. As energy is taken from the liquid in proximity to the colder product 19, then the energy is not replenished quickly enough to affect the product 19. This can be contrasted with the situation where the product 19 is passed through an opposing flow of hot liquid, and the temperature of the liquid surrounding the product 19 is thus maintained at the level of the hot liquid, thereby causing undesirable heat damage to the product 19.

In tests conducted by the inventors, when chicken is used as the product 19 and the liquid is water, and a flow provider 420 is used to match the speed of the liquid through the channel 404 to that of the conveyor 18 carrying the chicken through the channel 404, a water temperature of 90° C. in the channel 404 of the tank 401 has been found to be effective without causing any adverse organoleptic effects to the chicken.

Without wishing to be bound by theory, the present inventors hypothesize that when the chicken enters the tank 401 there will be an initial heat loss in the thin film of water surrounding the chicken as the chicken skin will be much colder than the surrounding water (as the chicken will typically be carried into the water in the tank 401 by the conveyor 18 from a chiller). This thin film is substantially maintained in position by the flow of water in the tank being matched in velocity to the speed of the chicken (the flow provider 420 matching the speed of the liquid through the channel 404 to that of the product 19 being carried by the conveyor 18) but this thin film is continuously being micro disturbed by the cavitation and micro scrubbing of the collapsing vacuum bubbles therefore the heat in this thin film is continuously being replenished by the surrounding water. Therefore the heat transfer through this thin film is high.

At a temperature of 90° C., the ultrasonic transducers 409 have been found to be less effective (presumably because they are operating outside of their nominal operating temperature), equivalent to reducing the power of the transducers 409. When the power of the transducers 409 is reduced there is a point at which it no longer has enough power to cause cavitation and the ultrasonic waves become pure pressure waves flooding the tank. The pressure waves act as compression and decompression waves when they meet a solid object so the chicken skin is continuously compressed and decompressed at a high frequency. When the chicken is compressed the feather follicles, cracks and crevices are compressed expelling any fluid inside these cavities and when the cavity is decompressed the cavity is refilled with water. This action is going on many thousand times per second so the surface and the crevices of the chicken skin are being vigorously rinsed. The transfer of heat is a great deal slower as the thin film of water around the chicken has a thermal gradient between the hot water and the chicken skin which on the decompression of the ultrasonic wave a proportion of the thin film of water is flushed into the crevices where it transfers its heat. On the compression part of the ultrasonic wave the skin is compressed and the cooler water is expelled back into the thin film surrounding the chicken so the transfer of heat is in many small packets. Because the amount of water going in and out of the crevices is small relative to the amount of water in the thin film, it remains substantially intact and continues to provide this thermal insulation function, thereby protecting the organoleptic qualities of the product 19. In some examples it may therefore be desirable to reduce the power supplied to the ultrasonic transducers 409 so as to maintain a protective thin film of liquid around the product 19, particularly if higher temperatures for the liquid in the tank 401 are selected.

In examples where the liquid is recirculated through the apparatus 400, for example via the flow provider 420, it may be desirable to run the ultrasonic transducers 409 for a time interval prior to running any product 19 through the apparatus 400 to reduce the concentration of dissolved gasses such as oxygen in the liquid. For example, if the apparatus 400 is activated/switched on from cold, the apparatus 400 may require a period of time for it to be brought to the selected operating temperature. For example, if the system is brought from an ambient temperature of 12° C. to an operating temperature of 75° C., this may take approximately 80 minutes. During this time, it may be desirable to operate the ultrasonic transducers 409 to reduce the dissolved gas concentration in the liquid. In addition, it may be desirable to run the ultrasonic transducers 409 for a selected time interval when the apparatus 400 has reached the selected operating temperature. For example, the ultrasonic transducers 409 may be operated at 50% power while the apparatus 400 is heating up, and then the transducers 409 may be operated for a further time interval, such as 60 minutes at 100% power, prior to running any product 19 through the apparatus. Tests have shown that doing so can dramatically increase the effect of ultrasonic cavitation in the liquid.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. For example, the function of the flow provider 420 may be distributed throughout the apparatus 400. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. For example, any of the features of the exampled described in relation to FIGS. 1 to 3, may be used with the example of FIGS. 4A to 6. Furthermore, equivalents and modifications not described above may also be employed without departing from the scope of the invention, which is defined in the accompanying claims.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

The activities and apparatus outlined herein may be controlled by a computer apparatus which may be implemented with fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

The invention claimed is:

1. An apparatus for disinfecting a product, the apparatus comprising:
   a tank arranged to provide ultrasonic energy to the product via a liquid for forcing microorganisms off the product and into the liquid;
   a reservoir arranged to receive and heat liquid transferred from the tank into the reservoir;
   wherein the temperature of the liquid in the reservoir is selected to disinfect the microorganisms forced off the products into the liquid;
   wherein the reservoir is configured to heat the liquid to a temperature equal to or greater than that of liquid in the tank, to a temperature of at least 75° C.;
   wherein the reservoir is configured to recirculate the liquid to the tank; and
   further comprising a flow through chiller for cooling the recirculated liquid.

2. The apparatus of claim 1 wherein the volume of the reservoir is larger than that of the tank so that the liquid remains in the reservoir for longer than in the tank, for example so that the liquid remains in the tank for less than 5 s, and in the reservoir for at least 30 s, for example at least 60 s, preferably wherein the dwell time and temperature of the liquid in the reservoir is selected to disinfect the microorganisms forced off the products into the liquid, for example so that the liquid remains in the reservoir at a temperature of at least 75° C. for at least 30 s.

3. The apparatus of claim 1 wherein the reservoir comprises at least one baffle arranged to slow the flow of liquid through the reservoir for encouraging the liquid to stratify.

4. A method for disinfecting products, the method comprising:
- holding a liquid for receiving microorganisms from the products in a tank in two regions separated by a barrier;
- carrying products into, along, and out of a flowpath through an open channel of liquid in the first region;
- delivering ultrasonic energy via the liquid in the second region and through the barrier to the products in the first region; and
- flowing the liquid through the channel in the first region at a velocity based on that of the product being carried through the liquid.

5. The method of claim 4 comprising adjusting the flow rate of liquid through the channel to match the velocity of the product being carried by the conveyor.

6. The method of claim 4 comprising adjusting the flow rate of liquid through the channel to provide a substantially laminar flow through the channel.

7. The method of claim 4 comprising holding the liquid in the second region at a relatively stationary velocity.

8. The method of claim 4 wherein the ultrasonic energy is delivered to the products by at least one ultrasonic transducer coupled to a wall of the tank inside the tank, preferably comprising a plurality of ultrasonic transducers arranged along the flowpath, preferably wherein the plurality of ultrasonic transducers are phase linked and/or synchronised.

9. The method of claim 4, further comprising transferring liquid from the tank comprising the barrier separating the two regions to a reservoir, and heating the liquid in the reservoir to a temperature selected to disinfect the microorganisms forced off the products into the liquid.

\* \* \* \* \*